United States Patent
Chen et al.

(10) Patent No.: US 10,669,255 B2
(45) Date of Patent: Jun. 2, 2020

(54) PYRROLE DERIVATIVES

(71) Applicant: HUA MEDICINE (SHANGHAI) LTD., Shanghai (CN)

(72) Inventors: Li Chen, Shanghai (CN); Yongguo Li, Shanghai (CN)

(73) Assignee: HUA MEDICINE (SHANGHAI) LTD., Shanghai (CN)

( * ) Notice: Subject to any disclaimer, the term of this patent is extended or adjusted under 35 U.S.C. 154(b) by 0 days.

(21) Appl. No.: 16/091,781

(22) PCT Filed: Apr. 6, 2016

(86) PCT No.: PCT/CN2016/078548
§ 371 (c)(1),
(2) Date: Oct. 5, 2018

(87) PCT Pub. No.: WO2017/173604
PCT Pub. Date: Oct. 12, 2017

(65) Prior Publication Data
US 2019/0100506 A1  Apr. 4, 2019

(51) Int. Cl.
C07D 401/06 (2006.01)
C07D 403/06 (2006.01)
C07D 207/325 (2006.01)

(52) U.S. Cl.
CPC ....... *C07D 401/06* (2013.01); *C07D 207/325* (2013.01); *C07D 403/06* (2013.01)

(58) Field of Classification Search
CPC .......................... C07D 207/325; C07D 401/06
See application file for complete search history.

(56) References Cited

U.S. PATENT DOCUMENTS

2016/0166575 A1  6/2016  Angiolini et al.

FOREIGN PATENT DOCUMENTS

| CN | 105061286 A | 11/2015 |
| WO | 2002/046166 A1 | 6/2002 |
| WO | 2003/059904 A1 | 7/2003 |
| WO | 2006/089700 A1 | 8/2006 |

OTHER PUBLICATIONS

Chen et al (2009), STN International (Columbus, Ohio) HCAPLUS database, Accession No. 2009: 433002.*
Zhang et al (2015), STN International (Columbus, Ohio) HCAPLUS database, Accession No. 2015: 665844.*
Brachet et al (2015), STN International (Columbus, Ohio) HCAPLUS database, Accession No. 2015: 1167594.*
Chinchilla et al., "Recent advances in Sonogashira reactions" Chem. Soc. Rev. 40(10): 5084-5121 (2011).
Corey et al., "A synthetic method for formyl → ethynyl conversion" Tetrahedron Lett. 13(36): 3769-3772 (1972).
Dekundy et al., "Effects of dopamine uptake inhibitor MRZ-9547 in animal models of Parkinson's disease" J. Neural Transm. 122(6):809-819 (2015).
Dutta et al., "Aerobic oxynitration of alkynes with t-BuONO and TEMPO" Organic Lett. 16(24): 6302-6305 (2014).
Emmitte, "mGlu5 negative allostereic modulators: a patent review (2010-2012)" Expert Opin. Ther. Pat. 23(4): 393-408 (2013).
Fischer, et al., "Ueber die Hydrazine der Brenztraubensaure" Berichte der deutschen chemischen Gesellschaft 16(2):2241-2245 (1883).
Fischer, et al., "Synthese von Indolderivaten" Berichte der deutschen chemischen Gesellschaft 17(1): 559-568 (1884).
Gasparini et al., "mGluR5 anatagonists: discovery, characterization and drug development" Curr. Opin. Drug Discov. Devel. 11(5): 655-665 (2008).
Guram et al., "Palladium-catalyzed aromatic aminations with in situ generated aminostannanes" J. Am. Chem. Soc. 116(17): 7901-7902 (1994).
Han, "Name reactions for homologations" John Wiley and Sons Pt. 1: 393-403 (2009).
Holmes et al., "Efficient synthesis of a complete donor/acceptor bis(aryl)diyne family" Synthetic Communications 33(14): 2447-2461 (2003).
Illa et al., "Reaction of C-silylated alpha-diazophosphines as nucleophiles toward carbonyl compounds: a mechanistic study and application to the synthesis of alkynes and alpha-hydroxyphosphonamides" J. Org. Chem. 71: 5320-5327 (2006).
King et al., "Palladium-catalyzed cross-coupling reactions in the synthesis of pharmaceuticals organometallics in process chemistry" Top. Organ. Met. 6: 205-245 (2004).
Knorr, "Synthese von Pyroolderivaten" Berichte der deutschen chemischen Gesellschaft 17(2): 1635-1642 (1884).
Lam et al., "New aryl/heteroaryl CN bond cross-coupling reactions via arylboronic acid/cupris acetate arylation" Tetrahedron Lett. 39(19): 2941-2944 (1998).
Li, et al., "Metabotropic glutamate recepter 5-negative allosteric modulators for the treatment of psychiatric and neurological disorders" Pharm. Pat. Anal. 2(6): 767-802 (2013).

(Continued)

*Primary Examiner* — Golam M Shameem
(74) *Attorney, Agent, or Firm* — McDonnell Boehnen Hulbert & Berghoff LLP

(57) ABSTRACT

Provided herein are compounds of the formula (I): as well as pharmaceutically acceptable salts thereof, wherein the substituents are as those disclosed in the specification. These compounds, and the pharmaceutical compositions containing them, are useful for the treatment or prevention of mGluR5 mediated disorders, such as acute and/or chronic neurological disorders, cognitive disorders and memory deficits, as well as acute and chronic pain.

(I)

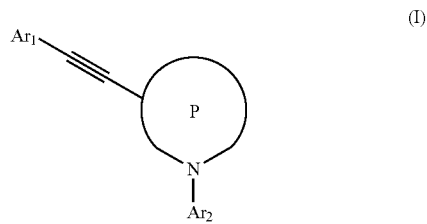

16 Claims, No Drawings

(56) References Cited

OTHER PUBLICATIONS

Negishi et al., "Direct synthesis of heteroarylethynes via palladium-catalyzed coupling of heteroaryl halide with ethynylzinc halides" 46(1): 209-214 (1997).

Niswender et al., "Metabotropic glutamate receptors: physiology, pharamacology, and disease" Ann. Rev. Pharmacol. Toxicol. 50: 295-322 (2010).

Paal, "Ueber die Derivate des Acetophenonacetessigesters und des Acetonylacetessigesters" Berichte der deutschen chemischen Gesellschaft 17: 2756-2767 (1884).

Paul et al., "Palladium-catalyzed formation of carbon-nitrogen bonds" J. Am. Chem. Soc. 116(13): 5969-5970 (1994).

Rocher et al., "mGluR5 negative allosteric modulators overview: a medicinal chemistry approach towards a series of novel therapeutic agents" Curr. Top. Med. Chem. 11(6): 680-695 (2011).

Rodriguez-Franco et al., "A mild and efficient method for the regioselective iodination of pyrazoles" Tetrahedron Lett. 42(5): 863-865 (2001).

Salanouve et al., "3-Methoxypyrazoles from 1,1-dimethoxyethene, few original results" Tetrahedron 68(15): 3165-3171.

Shigemoto et al., "Immunohistochemical localization of a metabotropic glutamate receptor, mGluR5, in the rat brain" Neuroscience Lett 163(1): 53-57 (1993).

Sonogashira, "Development of Pd—Cu catalyzed cross-coupling of terminal acetylenes with sp2-carbon halides" J. Organomet. Chem. 653: 46-69 (2002).

Chen, et al. "An Easy One-Pot Synthesis of Tetrasubstituted 3-Alkynylpyrroles via Multicomponent Coupling Reaction," SynLett, 5:828-832 (2009).

Xie, et al. "Pd-Catalyzed [3+2] cycloaddition of ketoimines with alkynes via directed sp3 C—H bond activation," Chem. Commun., 50(73):10699-0702 (2014).

Zhang, et al. "Gold-catalyzed cascade C—H/C—H cross-coupling/cyclization/alkynylation: an efficient access to 3-alkynylpyrroles", Organic & Biomolecular Chemistry, 13(21):5867-5870 (2015).

Brachet, et al., "Palladium-Catalyzed Regioselective Alkynylation of Pyrroles and Azoles under Mild Conditions: Application to the Synthesis of a Dopamine D-4 Receptor Agonist", Journal of Organic Chemistry, 80(15):7519-7529 (2015).

International Search Report & Written Opinion for International Application No. PCT/CN2016/078548, dated Jan. 10, 2017.

Worlikar et al., "Highly Substituted Indole Library Synthesis by Palladium-Catalyzed Coupling Reactions in Solution and on a Solid Support", J. Comb. Chem. 11(4):875-879 (2009).

* cited by examiner

PYRROLE DERIVATIVES

This application is a national stage application under 35 U.S.C. § 371 of International Application No. PCT/CN2016/078548, filed Apr. 6, 2016, the disclosure of which is explicitly incorporated by reference herein.

FIELD OF THE INVENTION

The present invention relates to compounds of general formula (I):

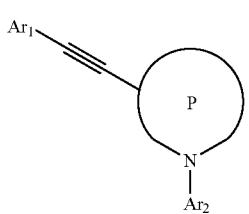

or a pharmaceutically acceptable salt thereof, and to pharmaceutical compositions comprising said compounds or a pharmaceutically acceptable salt thereof, wherein the definitions of $Ar_1$, $Ar_2$ and P are as defined below. The compounds and compositions disclosed herein are mGlu5 receptor antagonists useful for the treatment or prevention of mGluR5 mediated disorders, such as acute and/or chronic neurological disorders, cognitive disorders and memory deficits, as well as acute and chronic pain.

All documents cited or relied upon below are expressly incorporated herein by references.

BACKGROUND OF THE INVENTION

Glutamate is the most prominent neurotransmitter in the body, being present in over 50% of nervous tissue. Glutamate mediates its effects through two major groups of receptors: ionotropic and metabotropic. Ionotropic glutamate receptors are ion channel receptors which are often responsible for fast excitatory transmission. They are generally divided into N-methyl-D-aspartate (NMDA), α-amino-3-hydroxy-5-methyl-4-isoxazole propionic acid (AMPA) and kainite receptors. By contrast, metabotropic glutamate receptors (mGluRs) belong to the class C G-protein-coupled receptor (GPCR) protein family and are mainly involved in the modulation of fast excitatory transmission. As such, they are attractive therapeutic targets for treatment of disorders involving malfunction of glutamate signaling. The mGluRs are further divided into three groups (Group I, II and III) based on amino acid sequence homology, signal transduction mechanism and pharmacological properties. Group I receptors includes mGluR1 and mGluR5, Group II includes mGluR2 and mGluR3 and Group III includes mGluR4, mGluR6, mGluR7 and mGluR8. The Group I mGluR1 and mGluR5 receptors couple to G-proteins of the Gq family, Gq and G11, and their activation leads to activation of phospholipase C, resulting in the hydrolysis of membrane phosphatidylinositol (4, 5)-bisphosphate to diacylglycerol, which subsequently activates protein kinase C, and inositol trisphosphate, which in turn activates the inositol trisphosphate receptor to promote the release of intracellular calcium.

Anatomical studies demonstrate a broad and selective distribution of mGluRs in the mammalian nervous system. For example, mGlu5 receptors are abundantly expressed in the striatum, cortex, hippocampus, caudate-putamen and nucleus accumbens; see for example: Shigemoto, R., Nomura, S., Hidemitsu, S., et al. Neuroscience Lett. 163, 53-57, 1993. As these brain areas have been shown to be involved in emotion, motivational processes, learning and memory, as well as motor control, mGluR5 modulators have long been regarded as possessing therapeutic potential for a wide range of indications.

mGlu5 receptor antagonists can be used for modulating the activity of the mGlu5 receptor and for use in the treatment or prevention of mGluR5 mediated disorders, such as acute and/or chronic neurological disorders, cognitive disorders and memory deficits, acute and chronic pain, protection against drug or disease induced liver damage or failure, urinary inconsistence. Other diseases contemplated include cerebral ischemia, chronic neurodegeneration including Huntington's chorea, amyotrophic lateral sclerosis, Alzheimer's disease, Parkinson's disease, levodopa-induced dyskinesia in Parkinson's disease (PD-LID), psychiatric disorders, schizophrenia, mood disorders, emotion disorders, disorders of extrapyramidal motor function, obesity, disorders of pulmonary system and respiration, motor control and function, attention deficit disorders, concentration disorders, mental retardation (including mental retardation related to Fragile X syndrome), autism spectrum disorders (ASDs), pain disorders, neurodegenerative disorders, epilepsy, convulsive disorders, migraine, dyskinesia, eating disorders, vomiting, muscle spasms, urinary inconsistence, sleep disorders, sexual disorders, circadian disorders, drug withdrawal, drug addiction, compulsive disorders, anxiety, panic disorders, depression disorders, skin disorders, retinal ischemia, retinal degeneration, glaucoma, disorders associated with organ transplantation, asthma, ischemia and astrocytomas, diseases of the cardiovascular system, diseases of the gastrointestinal system such as gastroesophageal reflux disease (GERD) and irritable bowel syndrome, diseases of the endocrine system, diseases of the exocrine system, diseases of the skin, cancer and diseases of the ophthalmic system. The development and use of mGluR5 antagonists has been summarized in numerous review articles for example: Gasparini, F., Bilbe, G., Gomez-Mancilla, G., and Spooren, W., *Current Opinion in Drug Discovery & Development.* 11(5): 655-665, 2008; Rocher, J.-P., Bonnet, B., Boléa, C., et al., *Current Topics in Medicinal Chemistry.* 11, 680-695, 2011; Dekundy, A., Gravius, A., Hechenberger, M, et al., *J. Neural Transm.* 118, 1703-1716, 2011; Niswender, C. M. and Conn, P. J., *Annu Rev Pharmacol Toxicol.* 50, 295-322, 2010; Emmitte K A. mGlu5 negative allosteric modulators: a patent review (2010-2012). *Expert Opin Ther Pat.* 23(4):393-408, 2013 and Guiying Li, Morten Jørgensen and Brian M Campbell. Metabotropic glutamate receptor 5-negative allosteric modulators for the treatment of psychiatric and neurological disorders (2009-July 2013) Pharmaceutical Patent Analyst 2(6): 767-802.

SUMMARY OF THE INVENTION

The present invention is directed to compounds of the formula I, or a pharmaceutically acceptable salt thereof, pharmaceutical compositions containing them and to methods of treating diseases and disorders. The compounds and compositions disclosed herein are mGlu5 receptor antagonists useful for the treatment of mGluR5 mediated disorders, including acute and/or chronic neurological disorders, cognitive disorders and memory deficits, as well as acute and chronic pain.

DETAILED DESCRIPTION OF THE INVENTION

In an embodiment of the present invention, provided are compounds of formula I:

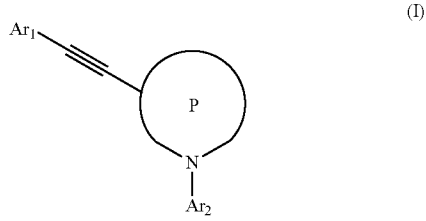

or a pharmaceutically acceptable salt thereof,
wherein:
$Ar_1$ is a 5- to 10-membered mono- or bicyclic heteroaryl ring that contains 1-3 heteroatoms selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —S($O_2$)-alkyl, —S($O_2$)-aryl, —$CH_2$-aryl, aryl, heteroaryl, —O—$CH_2$-aryl, —N($CH_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)$NH_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form an optionally substituted 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —S($O_2$)-alkyl, —S($O_2$)-aryl, —$CH_2$-aryl, aryl, heteroaryl, —O—$CH_2$-aryl, —N($CH_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)$NH_2$, —C(O)NH-alkyl, —C(O)N(alkyl)$_2$, —C(O)NH-cycloalkyl, —C(O)N(cycloalkyl)$_2$, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl, wherein the substituents may combine to form a 5-7 membered fused and optionally substituted carbacyclic or heterocyclic ring;
$Ar_2$ is a 5- to 10-membered mono- or bicyclic heteroaryl ring that contains 1-3 heteroatoms independently selected from the group consisting of N, O and S, wherein the 5- to 10-membered mono- or bicyclic heteroaryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —S($O_2$)-alkyl, —S($O_2$)-aryl, —O-alkyl-OH, —O-alkyl-O-alkyl, —$CH_2$-aryl, aryl, heteroaryl, —O—$CH_2$-aryl, —N($CH_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)$NH_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring, or a 5- to 10-membered mono- or bicyclic aryl ring, wherein the 5- to 10-membered mono- or bicyclic aryl ring is optionally substituted with 1-3 substituents independently selected from the group consisting of -alkyl, -halogen, —OH, —CN, nitro, —$CF_3$, —O—$CF_3$, —O-alkyl, —O-aryl, —S-alkyl, —S-aryl, —S(O)-alkyl, —S(O)-aryl, —S($O_2$)-alkyl, —S($O_2$)-aryl, —O-alkyl-OH, —O-alkyl-O-alkyl, —$CH_2$-aryl, aryl, heteroaryl, —O—$CH_2$-aryl, —N($CH_3$)$_2$, cycloalkyl, heterocycloalkyl, —C(O)-alkyl, —C(O)-cycloalkyl, —C(O)-heterocycloalkyl, —C(O)-aryl, —C(O)-heteroaryl, —C(O)O-alkyl, —C(O)O-cycloalkyl, —C(O)O-heterocycloalkyl, —C(O)O-aryl, —C(O)O-heteroaryl, —C(O)$NH_2$, —C(O)NH-alkyl, —C(O)N(alkyl)$_2$, —C(O)NH-cycloalkyl, —C(O)N(cycloalkyl)$_2$, —C(O)NH-heterocycloalkyl, —C(O)N(heterocycloalkyl)$_2$, —C(O)NH-aryl, —C(O)N(aryl)$_2$, —C(O)NH-heteroaryl, —C(O)N(heteroaryl)$_2$, and substituted lower alkyl wherein the substituents may combine to form an optionally substituted 5-7 membered fused carbacyclic or heterocyclic ring;
P is a heteroaryl ring selected from

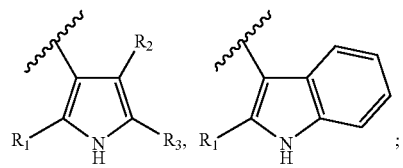

$R_1$, $R_2$ and $R_3$ are independently selected from —H, halogen, —OH, —CN, nitro, alkyl, alkoxy, —$CF_3$, —$OCF_3$, —$CH_2$-aryl, phenyl, heteroaryl, alkanoyl, —O-aryl, —O—$CH_2$-aryl, —N($CH_3$)$_2$, —C(O)-cycloalkyl, —C(O)-heterocycloalkyl. —C(O)O-alkyl, —C(O)O-aryl, wherein the substituents may combine to form an optionally substituted 5-7 membered fused carbacyclic or heterocyclic ring.

In a further embodiment of the present invention, provided is a compound according to formula (I)

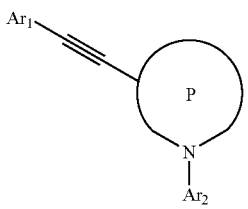

(I)

or a pharmaceutically acceptable salt thereof,
wherein:
$Ar_1$ is 2-pyridinyl optionally substituted with 1 or 2 substituents independently selected from —$C_1$-$C_4$-alkyl, wherein —$C_1$-$C_4$-alkyl includes, but are not limited to, methyl, ethyl, n-propyl, iso-propyl, n-butyl, iso-butyl, tert-butyl, or
$Ar_1$ is 4-pyridinyl, pyrimidinyl or phenyl;
$Ar_2$ is a 5- to 10-membered mono- or bicyclic aryl or heteroaryl ring that contains 1-3 heteroatoms independently selected from the group consisting of N, O and S, wherein the 5- to 10-membered ring system is optionally substituted with 1, 2 or 3 substituents independently selected from —$C_1$-$C_4$-alkyl, halogen, —OH, —CN, nitro, —$CF_3$, —$OCF_3$, —O—$C_1$-$C_4$-alkyl, —$SCH_3$, —S(O)—$CH_3$, —S($O_2$)—$CH_3$, —$CO_2CH_3$, —C(O)$NH_2$, —C(O)NH($CH_3$), —C(O)N($CH_3$)$_2$, phenyl, wherein the —$C_1$-$C_4$-alkyl is preferably methyl, ethyl, n-propyl, iso-propyl, n-butyl, iso-butyl, tert-butyl; the —O—$C_1$-$C_4$-alkyl is preferably methoxy, ethoxy, n-propoxy, iso-propoxy, n-butoxy, iso-butoxy, tert-butoxy,
wherein the 5- to 10-membered ring system is preferably phenyl;
P is a heteroaryl ring selected from

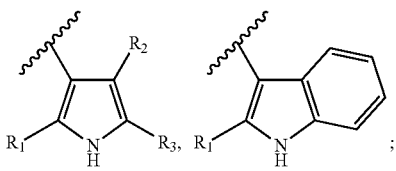

$R_1$, $R_2$ and $R_3$ are independently selected from —H, halogen, —OH, —CN, nitro, alkyl, alkoxy, —$CF_3$, —$OCF_3$, —$CH_2$-aryl, phenyl, heteroaryl, alkanoyl, —O-aryl, —O—$CH_2$-aryl, —N($CH_3$)$_2$, —C(O)-cycloalkyl, —C(O)-heterocycloalkyl, —C(O)O-alkyl, —C(O)O-aryl, wherein the substituents may combine to form an optionally substituted 5-7 membered fused carbacyclic or heterocyclic ring.

In a further embodiment of the present invention, provided is a compound according to formula (Ia)

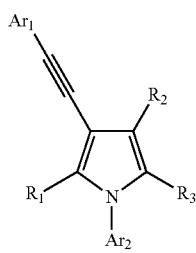

(Ia)

or a pharmaceutically acceptable salt thereof,
wherein:
$Ar_1$ is a 5- to 10-membered mono- or bicyclic heteroaryl ring that contains 1-3 heteroatoms selected from the group consisting of N, O and S, wherein the 5- to 10-membered ring system is optionally substituted with 1-3 substituents independently selected from alkyl, —F, —Cl, —Br, —OH, —CN, nitro, alkoxy, —$CF_3$, —O—$CF_3$, —S($CH_3$), —O-alkyl, —S-alkyl, —S(O)-alkyl, —S($O_2$)-alkyl, —S($O_2$)-aryl, —$CH_2$-aryl, heteroaryl, alkanoyl, —O-aryl, —O—$CH_2$-aryl, —N($CH_3$)$_2$, cycloalkyl, heterocycloalkyl, —C(O)-cycloalkyl, —C(O)-heterocycloalkyl, wherein the substituents may combine to form an optionally substituted 5-7 membered fused carbacyclic or heterocyclic ring, or
a 5- to 10-membered mono- or bicyclic aryl ring, wherein the 5- to 10-membered aryl ring is optionally substituted with 1-3 substituents independently selected from alkyl, —F, —Cl, —Br, —OH, —CN, nitro, alkoxy, —$CF_3$, —$OCF_3$, —S($CH_3$), —O-alkyl, —S-alkyl, —S(O)-alkyl, —S($O_2$)-alkyl, —S($O_2$)-aryl, —$CH_2$-aryl, heteroaryl, alkanoyl, —O-aryl, —O—$CH_2$-aryl, —N($CH_3$)$_2$, cycloalkyl, heterocycloalkyl, —C(O)-cycloalkyl, —C(O)-heterocycloalkyl, wherein the substituents may combine to form a 5-7 membered fused and optionally substituted carbacyclic or heterocyclic ring;
$Ar_2$ is a 5- to 10-membered mono- or bicyclic heteroaryl ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —$CF_3$, —$OCF_3$, —S($CH_3$), —$OCH_3$, —S-alkyl, —S(O)-alkyl, —S($O_2$)-alkyl, —S($O_2$)-aryl, —$CH_2$-aryl, heteroaryl, alkanoyl, —O-aryl, —O—$CH_2$-aryl, —N($CH_3$)$_2$, cycloalkyl, heterocycloalkyl, —C(O)-cycloalkyl, —C(O)-heterocycloalkyl, or substituted lower alkyl wherein the substituents may combine to form an optionally substituted 5-7 membered fused carbacyclic or heterocyclic ring,
or a 5- to 10-membered mono- or bicyclic aryl ring, wherein the 5- to 10-membered ring system is optionally substituted with 1-3 substituents independently selected from alkyl, —F, —Cl, —Br, —OH, —CN, nitro, alkoxy, —$CF_3$, —$OCF_3$, —S($CH_3$), —$OCH_3$, —S-alkyl, —S(O)-alkyl, —S($O_2$)-alkyl, —S($O_2$)-aryl, —$CH_2$-aryl, heteroaryl, alkanoyl, —O-aryl, —O—$CH_2$-aryl, —N($CH_3$)$_2$, cycloalkyl, heterocycloalkyl, —C(O)-cycloalkyl, —C(O)-heterocycloalkyl, or substituted lower alkyl wherein the substituents may combine to form an optionally substituted 5-7 membered fused carbacyclic or heterocyclic ring;
$R_1$, $R_2$ and $R_3$ are independently selected from —H, halogen, —OH, —CN, nitro, alkyl, alkoxy, —$CF_3$, —$OCF_3$, —$CH_2$-aryl, phenyl, heteroaryl, alkanoyl, —O-aryl, —O—$CH_2$-aryl, —N($CH_3$)$_2$, —C(O)-cycloalkyl, —C(O)-heterocycloalkyl, —C(O)O-alkyl, —C(O)O-aryl, wherein the substituents may combine to form an optionally substituted 5-7 membered fused carbacyclic or heterocyclic ring.

In another embodiment, provided is a compound according to formula Ia, or a pharmaceutically acceptable salt thereof, wherein:
$Ar_1$ is a substituted or unsubstituted ring selected from the following list:

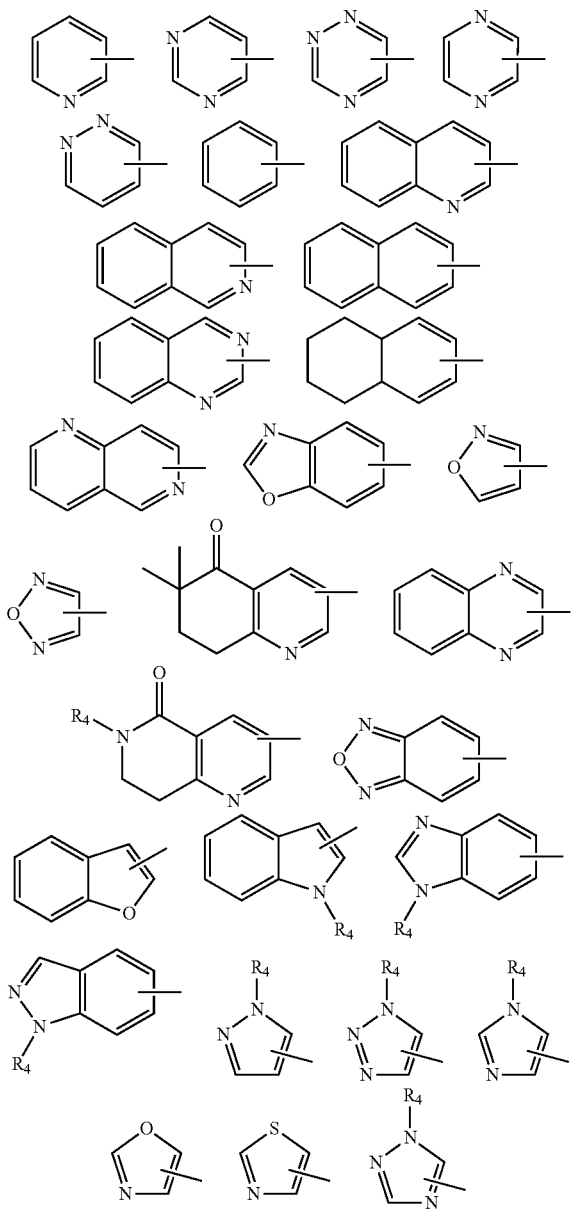

R₄ is —H or lower alkyl;
Ar₂ is a 5- to 10-membered mono- or bicyclic ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —CF₃, —OCF₃, —S(CH₃), —OCH₃, —S-alkyl, —S(O)-alkyl, —S(O₂)-alkyl, —S(O₂)-aryl, —CH₂-aryl, heteroaryl, alkanoyl, —O-aryl, —O—CH₂-aryl, —N(CH₃)₂, cycloalkyl, heterocycloalkyl, —C(O)-cycloalkyl, —C(O)-heterocycloalkyl, or substituted lower alkyl wherein the substituents may combine to form an optionally substituted 5-7 membered fused carbacyclic or heterocyclic ring, or
a 5- to 10-membered mono- or bicyclic aryl ring, wherein the 5- to 10-membered ring system is optionally substituted with 1-3 substituents independently selected from alkyl, halogen, —OH, —CN, nitro, alkoxy, —CF₃, —OCF₃, —S(CH₃), —OCH₃, —S-alkyl, —S(O)-alkyl, —S(O₂)-alkyl, —S(O₂)-aryl, —CH₂-aryl, heteroaryl, alkanoyl, —O-aryl, —O—CH₂-aryl, —N(CH₃)₂, cycloalkyl, heterocycloalkyl, —C(O)-cycloalkyl, —C(O)-heterocycloalkyl, or substituted lower alkyl wherein the substituents may combine to form an optionally substituted 5-7 membered fused carbacyclic or heterocyclic ring;

$R_1$, $R_2$ and $R_3$ are independently selected from —H, halogen, —OH, —CN, nitro, alkyl, alkoxy, —CF₃, —OCF₃, —CH₂-aryl, phenyl, heteroaryl, alkanoyl, —O-aryl, —O—CH₂-aryl, —N(CH₃)₂, —C(O)-cycloalkyl, —C(O)-heterocycloalkyl, —C(O)O-alkyl, —C(O)O-aryl, wherein the substituents may combine to form an optionally substituted 5-7 membered fused carbacyclic or heterocyclic ring.

In a further embodiment, provided is a compound according to formula Ia, or a pharmaceutically acceptable salt thereof, wherein:
$Ar_1$ is 2-pyridinyl;
$Ar_2$ is optionally mono- or disubstituted mono- or bicyclic aryl, optionally mono- or disubstituted mono- or bicyclic heteroaryl;
$R_1$, $R_2$ and $R_3$ are independently selected from —H, halogen, —OH, —CN, nitro, alkyl, alkoxy, —CF₃, —OCF₃, —CH₂-aryl, phenyl, heteroaryl, alkanoyl, —O-aryl, —O—CH₂-aryl, —N(CH₃)₂, —C(O)-cycloalkyl, —C(O)-heterocycloalkyl, —C(O)O-alkyl, —C(O)O-aryl, wherein the substituents may combine to form an optionally substituted 5-7 membered fused carbacyclic or heterocyclic ring.

In a further embodiment of the present invention, provided is a compound according to formula Ia, or a pharmaceutically acceptable salt thereof, wherein:
$Ar_1$ is 2-pyridinyl, 4-pyridinyl, pyrimidinyl or phenyl;
$Ar_2$ is a 5- to 10-membered mono- or bicyclic aryl or heteroaryl ring that contains 1-3 heteroatoms independently selected from the group consisting of N, O and S, wherein the 5- to 10-membered ring system is optionally substituted with 1-3 substituents independently selected from —C₁-C₄-alkyl, halogen, —OH, —CN, nitro, —CF₃, —OCF₃, —O—C₁-C₄-alkyl, —SCH₃, —S(O)—CH₃, —S(O₂)—CH₃, —CO₂CH₃, —C(O)NH₂, —C(O)NH(CH₃), —C(O)N(CH₃)₂, phenyl, wherein the —C₁-C₄-alkyl is preferably methyl, ethyl, n-propyl, iso-propyl, n-butyl, iso-butyl, tert-butyl; the —O—C₁-C₄-alkyl is preferably methoxy, ethoxy, n-propoxy, iso-propoxy, n-butoxy, iso-butoxy, tert-butoxy,
wherein the 5- to 10-membered ring system is preferably phenyl;
$R_1$, $R_2$ and $R_3$ are independently selected from —H, halogen and —CH₃.

In a further embodiment of the present invention, provided is a compound according to formula Ib:

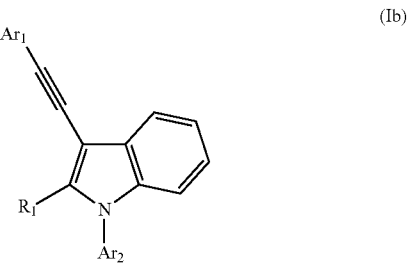

(Ib)

or a pharmaceutically acceptable salt thereof, wherein:
Ar$_1$ is an unsubstituted or substituted ring selected from the following list:

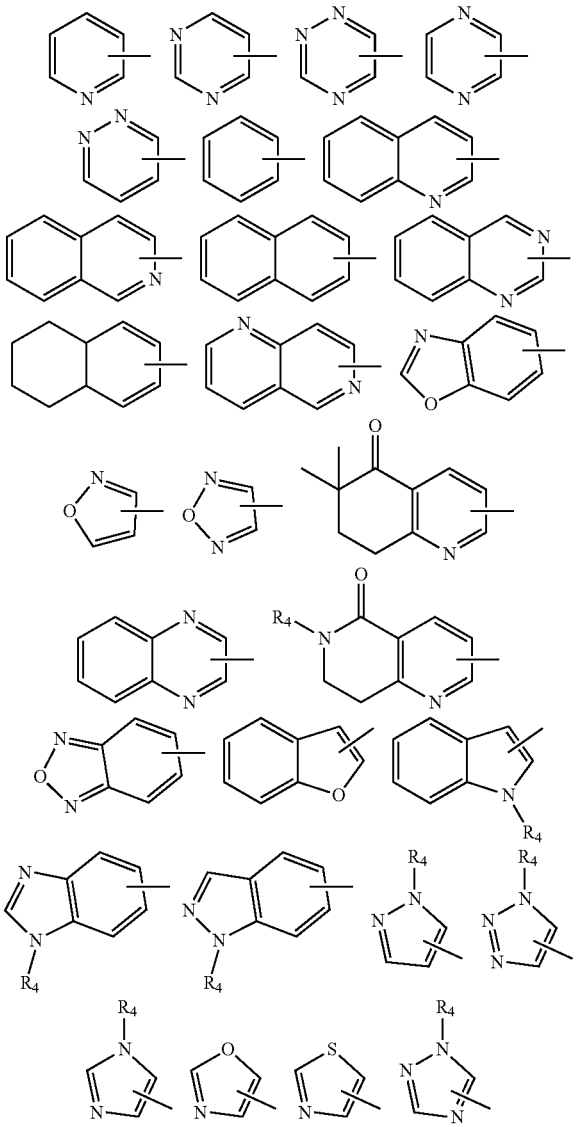

R$_4$ is —H or lower alkyl
Ar$_2$ is a 5- to 10-membered mono- or bicyclic heteroaryl ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl or
a 5- to 10-membered mono- or bicyclic aryl ring, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl;

R$_1$, R$_2$ and R$_3$ are independently selected from —H, halogen, —OH, —CN, nitro, alkyl, alkoxy, —CF$_3$, —OCF$_3$, —CH$_2$-aryl, phenyl, heteroaryl, alkanoyl, —O-aryl, —O—CH$_2$-aryl, —N(CH$_3$)$_2$, —C(O)-cycloalkyl, —C(O)-heterocycloalkyl, —C(O)O-alkyl, —C(O)O-aryl.

In a further embodiment, provided is a compound according to formula Ib, or a pharmaceutically acceptable salt thereof, wherein:
Ar$_1$ is 2-pyridinyl or substituted 2-pyridinyl;
Ar$_2$ is optionally mono- or disubstituted mono- or bicyclic aryl, optionally mono- or disubstituted mono- or bicyclic heteroaryl;
R$_1$ is H.

In a further embodiment of the present invention, provided is a compound according to formula Ib, or a pharmaceutically acceptable salt thereof, wherein:
Ar$_1$ is 2-pyridinyl optionally substituted with 1 or 2 substituents independently selected from C$_1$-C$_4$-alkyl, wherein C$_1$-C$_4$-alkyl includes, but are not limited to, methyl, ethyl, n-propyl, iso-propyl, n-butyl, iso-butyl, tert-butyl;
Ar$_2$ is a 5- to 10-membered mono- or bicyclic aryl or heteroaryl ring that contains 1, 2, or 3 heteroatoms independently selected from the group consisting of N, O and S, wherein the 5- to 10-membered ring system is optionally substituted with 1, 2 or 3 substituents independently selected from —C$_1$-C$_4$-alkyl, —F, —Cl, —Br, —OH, —CN, nitro, —CF$_3$, —OCF$_3$, —O—C$_1$-C$_4$-alkyl, —SCH$_3$, —S(O)—CH$_3$, —S(O$_2$)—CH$_3$, —CO$_2$CH$_3$, —C(O)NH$_2$, —C(O)NH(CH$_3$), —C(O)N(CH$_3$)$_2$, phenyl, wherein the —C$_1$-C$_4$-alkyl is preferably methyl, ethyl, n-propyl, iso-propyl, n-butyl, iso-butyl, tert-butyl; the —O—C$_1$-C$_4$-alkyl is preferably methoxy, ethoxy, propoxy, iso-proxy, n-butoxy, iso-butoxy, tert-butoxy, wherein the 5- to 10-membered ring system is preferably phenyl;
R$_1$ is H.

In a still further embodiment of the present invention, provided is a pharmaceutical composition, comprising a therapeutically effective amount of a compound according to formula I or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond of two to twenty carbon atoms, preferably two to sixteen carbon atoms, more preferably two to ten carbon atoms.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further unless indicated otherwise in the Examples or claims below. Each substituent can independently be, alkyl, alkoxy, halogen, amino, hydroxyl or oxygen (O=) unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, iso-propyl, n-butyl, iso-butyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylaminocarbonyloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of such groups include, but are not limited to, pyrimidinyl, pyridyl, indoyl, quinolinyl, pyridon-2-yl, isoquinolinyl, 5,6,7,8-tetrahydroquinolinyl, thienyl, furanyl, imidazolyl, pyrazolyl, thiazolyl, isothiazolyl, oxazolyl, oxadiazolyl, thiadiazolyl, pyrazolidinyl, pyrazinyl, pyridazinyl, thianaphthyl, benzofuranyl, isobenzofuranyl, oxyindolyl, isoindolyl, indazolyl, indolinyl, 7-azaindolyl, benzopyranyl, coumarinyl, isocoumarinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and the like.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arylcarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—, and "alkanoyl" means alkyl-CO—. Alkoxy substituent groups or alkoxy-containing substituent groups may be substituted by, for example, one or more alkyl groups, with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

As used herein, the term "pharmaceutically acceptable salt" means any pharmaceutically acceptable salt of the compound of formula I. Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions or of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster.

The present compounds of formula I can be prepared by the methods described below, by the methods given in the schemes or in the examples. Appropriate reaction conditions for the individual reaction steps are known to a person skilled in the art. The reaction sequence is not limited to the one displayed in the schemes, however, depending on the starting materials and their respective reactivity, the sequence of reaction steps can be freely altered. Starting materials are either commercially available or can be prepared by methods analogous to the methods given below, by methods described in the examples, or by methods known in the art.

The present compounds of formula I can be prepared by the following schemes described below.

Scheme 1

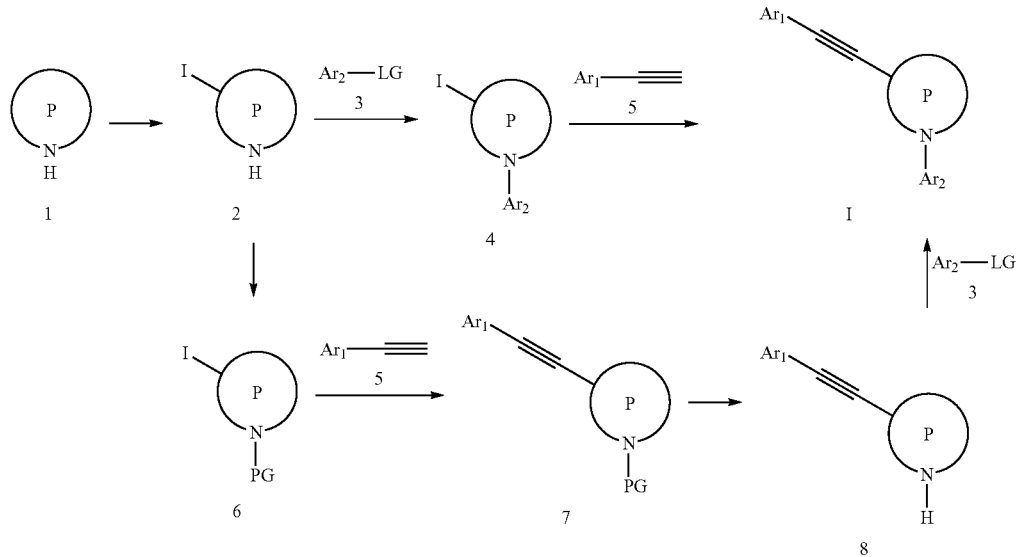

In scheme 1 compounds of formula 1 are known, and in many cases, commercially available compounds or can be prepared using well established methodology. For example, P are pyrrole or benzopyrrole (indole) derivatives are commercially available from several suppliers including Sigma-Aldrich. In case compound of formula 1 are not commercially available, it can be synthesized through the well-established methods like Paal-Knorr Pyrrole Synthesis and Fischer Indole Synthesis. The Paal-Knorr Pyrrole Synthesis is the condensation of a 1,4-dicarbonyl compound with an excess of a primary amine or ammonia to give a pyrrole (Paal, C., *Berichte der deutschen chemischen Gesellschaft.* 17: 2756, 1884; Knorr, L., *Berichte der deutschen chemischen Gesellschaft* 17: 2863, 1884). The Fischer indole synthesis is a chemical reaction that produces the aromatic heterocycle indole from a (substituted) phenylhydrazine and an aldehyde or ketone under acidic conditions (Fischer, E.; Jourdan, F.). Ueber die Hydrazine der Brenztraubensäure. *Berichte der Deutschen Chemischen Gesellschaft.* 16 (2): 2241-2245, 1883; Fischer, E.; Hess, O. *Synthese von Indolderivaten. Berichte der Deutschen Chemischen Gesellschaft.* 17 (1): 559-568, 1884).

Conversion of compounds of formula 1 to the iodides 2 may be carried out with iodide in alkaline solution ($I_2$/KOH) or by the addition of hydrogen peroxide to a solution containing potassium iodide. Other iodinating systems to have been used include $I_2$/$HIO_3$, $I_2$/HgO, $I_2$/$AgOCOCF_3$, and N-iodosuccinimide (NIS) (*Tetrahedron Letters,* 42 (15), 863-865, 2001; *Tetrahedron Letters,* 68 (15), 3165-3171, 2012).

In scheme 1 compounds of formula 5, for example, $Ar_1$=2-pyridinyl or 3-pyridinyl are available from several suppliers including Sigma-Aldrich. In the case that commercial supplies are not readily available, aryl- and het-eroaryl alkynes can be prepared from the corresponding aryl or heteroaryl carboxaldehydes using the Corey-Fuchs procedure (Corey, E. J. and Fuchs, P. L., *Tetrahedron Lett.* 3769, 1972; reviewed in: Han, Xiaojun. Editor(s): Li, Jie Jack. *Name Reactions for Homologations.* (Pt. 1), 393-403, 2009, Publisher: John Wiley & Sons, Inc.). Alternatively, aryl and heteroaryl carboxaldehydes may be converted to aryl or heteroaryl alkynes by treatment with C-silylated-diazophosphines under neutral conditions (Ona, I., Xavier, B., Cazoria, A. M., et al., *Journal of Organic Chemistry,* 71, 5320, 2006).

In cases where the appropriate carboxaldehydes are not readily available, aryl or heteroaryl aryl alkynes may also be prepared from aryl or heteroaryl compounds functionalized with groups capable of undergoing transition metal catalyzed cross-coupling reactions with alkynes. Those skilled in the art will appreciate how to select the appropriate reaction partners. For example 3-alkynyl pyridine can be synthesized from either 3-bromopyridine or 3-trifluoromethanesulfonyl pyridine through reactions with suitably functionalized alkynes catalyzed by transition metals, followed by deprotection of terminal alkynes bearing a protecting group at the terminal position. In the event the protecting group is trimethylsilyl (TMS), the compound may be treated with an aqueous base, for example potassium hydroxide or tetrabutylammonium fluoride (TBAF) in methanol to effect its removal. In the case where the alkyne is formed through a transition metal catalyzed reaction between an aryl or heteroaryl ring bearing a suitable functionality for cross coupling reactions, for example a bromide, and 2-methyl-3-butyne-2-ol, deprotection to give a terminal alkyne can be achieved through heating in a suitable solvent, for example toluene, in the presence of catalytic amounts of a base, for example sodium hydride. The following references are among the many examples of such transformations in the published literature: Uttam Dutta, Soham Maity, Rajesh Kancherla, and Debabrata Maiti, *Organic Letters,* 16(24), 6302-6305, 2014; Holmes, B. T., Pennington, W. T., Hanks, T. W., *Synthetic Communications,* 33, 2447-2461, 2003; Negishi, E.-i., Xu, C., Tan, Z., Kotora, M., *Heterocycles,* 46, 209-214, 1997. One common variant is known as the Sonogashira coupling reaction, reviewed in Chinchilla, R., Nájera, C., Recent Advances in Sonogashira reactions, *Chemical Society Reviews*, 40, 5084-5121, 2011.

Compound of formula 2 could go through two pathways to get the final product of formula I.

(1) In scheme 1 compound of formula 3 in which LG is a leaving group, which can be halogen like F, Cl, Br and I or B(OH)$_2$. Reaction condition for compounds of formula 2 and 3 to get the compound of formula 4 depending on the LG types, 1) for example, when LG is B(OH)$_2$, compounds of formula of 2 and 3 go through Chan-Lam Coupling reaction in an suitable inert solvent, such as DCM in the presence of catalyst copper (II) like Cu(OAC)$_2$ at a suitable temperature, for example room temperature in air, after reaction is completed the newly formed compound of formula 4 can be isolated using conventional technics, for example by filtering and concentrating under vacuo, the reaction residue was purified through chromatography over silica gel (P. Y. S. Lam, C. G. Clark, S. Saubern, J. Adams, M. P. Winters, D. M. T. Chan, A. Combs, *Tetrahedron Lett.*, 39, 2941-2944, 1998); 2) for example, when LG is halogen like F, Cl, Br or I, compounds of formula 2 and 3 go through SNAr reaction or Buchwald-Hartwig Amination in an suitable inert solvent, appropriate reaction conditions for the individual reaction steps are known to a person skilled in the art (Paul, F.; Patt, J.; Hartwig, J. *J. Am. Chem. Soc.*, 116, 5969, 1994; Guram, A.; Buchwald, S. *J. Am. Chem. Soc.*, 116, 7901, 1994). After reaction is completed and the newly formed compound of formula 4 can be isolated using conventional technics, for example by quenching the reaction with an aqueous solution followed by extraction of the products into an organic solvent, washing with brine, drying and chromatography over silica gel, if necessary.

Reaction of compound of formula 4 and aryl or heteroaryl alkyne 5 to form the final product of formula I can be achieved by Sonogashira coupling of the alkyne 5 and halohydrocarbon 4 in a suitable inert solvent, for example THF, by adding Pd(PPH$_3$)$_2$Cl$_2$, Et$_3$N and CuI, then the reaction mixture microwaved at a medium temperature, for example 90° C., after reaction is completed and the newly formed compound I can be isolated using conventional technics, for example the reaction mixture was concentrated to dryness and the residue was purified by pre-HPLC to afford the final product of formula I (Sonogashira, K. "Development of Pd—Cu catalyzed cross-coupling of terminal acetylenes with sp$^2$-carbon halides", *J. Organomet. Chem.* 653: 46-49, 2002; King, A. O.; Yasuda, N. "Palladium-Catalyzed Cross-Coupling Reactions in the Synthesis of Pharmaceuticals Organometallics in Process Chemistry", *Top. Organomet. Chem.* 6: 205-245, 2004).

(2) In Scheme 1 compound of formula 6, in which PG is a protecting group, for example a 1,1-dimethylethoxycarbonyl (Boc) group, conditions for the removal of the protecting group to give the compound of formula 8, will depend on the particular choice of protecting group employed. Skilled organic chemists will be familiar with the various potential protecting and the procedures for their removal. In this regard, reference to a compendium of protecting groups such as Wuts, P. G. and Greene, T. W., Greene's Protective Groups in Organic Synthesis, 4th ed., cited above may be useful. In one convenient implementation, a Boc ((1,1-dimethylethoxy)carbonyl) group may be used. In this case, its removal to give a compound of formula 8 may be readily achieved by treatment with an acid, for example trifluoroacetic acid (TFA) in a suitable solvent, for example dichloromethane followed by a conventional workup.

Reaction of compound of formula 6 and aryl or heteroaryl alkyne 5 to form compound of formula 7 can be achieved by Sonogashira coupling just as described above. Compound of formula 7 may be treated with an acid, for example trifluoroacetic acid (TFA) in a suitable solvent, for example dichloromethane to effect the removal of protecting group 1,1-dimethylethoxycarbonyl (Boc), then followed by a conventional workup to get compound of formula 8. Reaction of compound of formula 8 and compound of formula 3 to form final product of formula I just as described above.

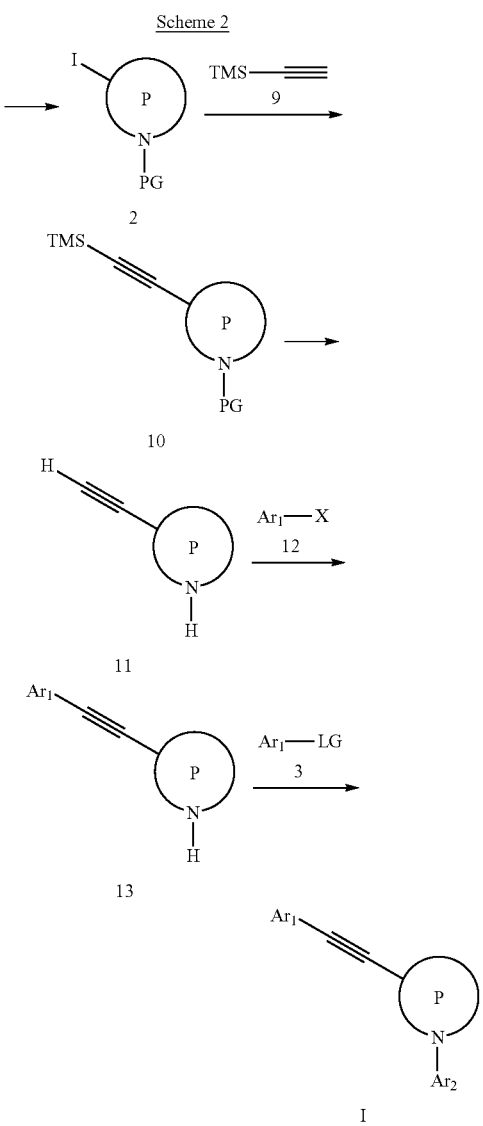

Scheme 2

An alternative method for the preparation of compounds of formula I is shown in Scheme 2. Iodides 2 can be achieved by nucleophilic substitution reaction, like combination of a solution of 1 to a iodination reagent, for example N-iodosuccinimide (NIS) in a suitable inert solvent, for example, acetone at appropriate temperature. Such reactions may be worked up using common procedures, for example, the reaction mixture was concentrated under vacuo and the residue was purified by silica gel chromatography, if necessary.

Reaction of compound of formula 2 and ethynyltrimethylsilane 9 to form compound of formula 10 can be achieved by Sonogashira coupling of the alkyne 9 and halohydrocarbon 2 in a suitable inert solvent, for example CH₃CN, by adding Pd(PPH₃)₂Cl₂, Et₃N and CuI, then reaction at a medium temperature, for example 70° C., after reaction is completed and the newly formed compound of formula 10 can be isolated using conventional technics, for example the reaction mixture was filtered and concentrated then purified by chromatograph column. Compound of formula 10 may be treated with an aqueous base, for example potassium hydroxide or tetrabutylammonium fluoride (TBAF) in MeOH to effect the removal of protecting group trimethylsilyl (TMS) to afford compound of formula 11, which reacted with compound of formula 12 through Sonogashira coupling in a suitable inert solvent, for example CH₃CN, by adding Pd(PPH₃)₂Cl₂, Et₃N and CuI, then the reaction mixture was stirred at appropriate temperature, for example 90° C., after reaction is completed and the newly formed compound of formula 13 can be isolated using conventional technics, the mixture was filtered and concentrated by vacuo to give the crude product which was purified by silica gel chromatography. Just as described in Scheme 1, reaction of compounds of formula 13 and 3 to form the final product of formula I.

The preparations of compounds of formula I (for P is pyrrole and 2, 5-dimethyl pyrrole) are show in Scheme 3 and Scheme 4, the much more detailed information will be presented in the examples below.

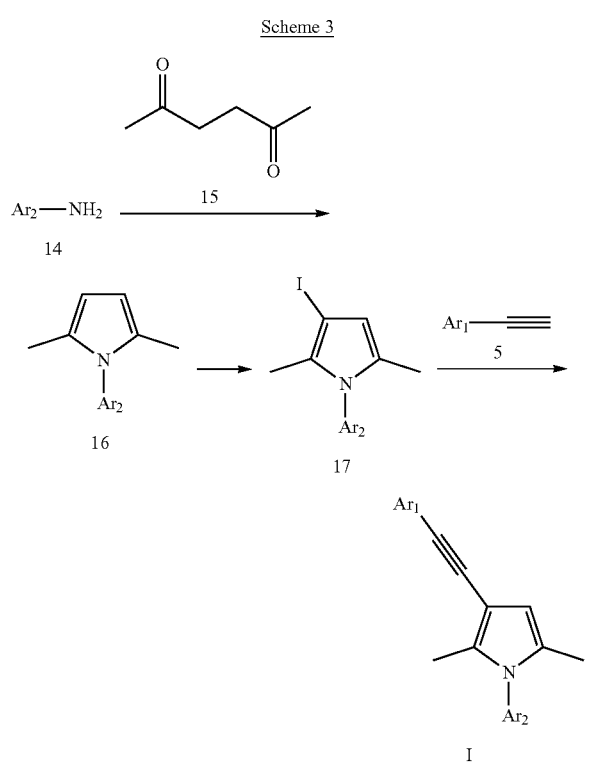

The invention will now be further described in the Examples below, which are intended as an illustration only and do not limit the scope of the invention.

EXAMPLES

Example 1

Preparation of 2-ethynyl-pyrimidine

Experimental Section:
Procedure for Preparation of 3:

To a solution of 1 (5.0 g, 31.45 mmol) and 2 (3.40 g, 34.6 mmol) in 30 mL of Et₃N was added CuI (0.6 g, 3.15 mmol) and Pd(PPh₃)₄ (1.8 g, 1.55 mmol). The resulting mixture was protected with N₂ atmosphere, and then was stirred for 48 hours at room temperature. TLC showed the starting material was consumed. The reaction mixture was then concentrated in vacuo. The crude product was purified by silica gel column chromatography to give product 3 (3.5 g, yield: 63.1%).

Procedure for Preparation of 4:

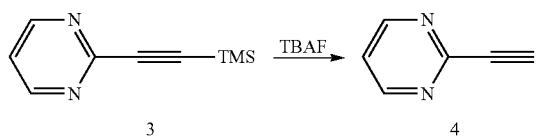

To a solution of 3 (3.2 g, 18.15 mmol) in 10 mL THF was added 1M of TBAF (18.15 mL, 18.15 mmol) over 3 minutes. TLC showed the starting material was consumed. The reaction mixture was then concentrated in vacuo. The crude product was purified by silica gel column chromatography to give product 4 (1.3 g, yield: 68.8%).

LCMS: nm/z, 105 (M+H)$^+$.

Example 2

Preparation of 4-ethynyl-pyridine

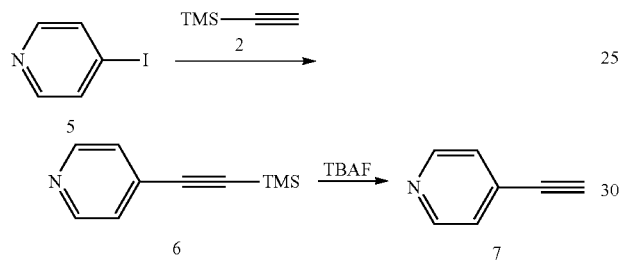

Experimental Section:
Procedure for Preparation of 6:

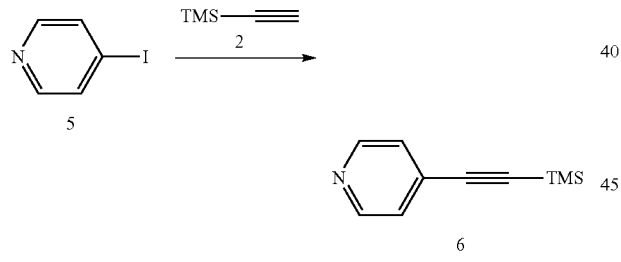

To a solution of 5 (5.0 g, 24.39 mmol) and 2 (2.64 g, 26.8 mmol) in 100 mL of Et$_3$N was added Pd(PPh$_3$)$_4$ (1.40 g, 1.22 mmol) and CuI (0.46 g, 2.44 mmol). The reaction mixture was protected by N$_2$ atmosphere, and was stirred at room temperature for 48 hours. TLC showed that the starting material was consumed. The reaction mixture was then concentrated in vacuo. The resulting crude product was purified by silica gel column chromatography to give the target product 6 (3.0 g, yield: 70.2%).

Procedure for Preparation of 7:

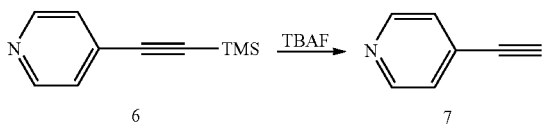

To a solution of 6 (3.0 g, 17.14 mmol) in 10 mL THF was added 17.11 mL 1M of TBAF (17.11 mL, 17.11 mmol) over 3 minutes. TLC analysis showed complete conversion of starting material to a major product. The reaction mixture was then concentrated in vacuo. The crude product was purified by silica gel column chromatography to give product 7 (1.2 g, yield: 68.0%).

LCMS: m/z 104 (M+H)$^+$.

Example Compound 1

Preparation of 3-iodo-5-(3-(pyridin-2-ylethynyl)-1H-indol-1-yl)benzonitrile

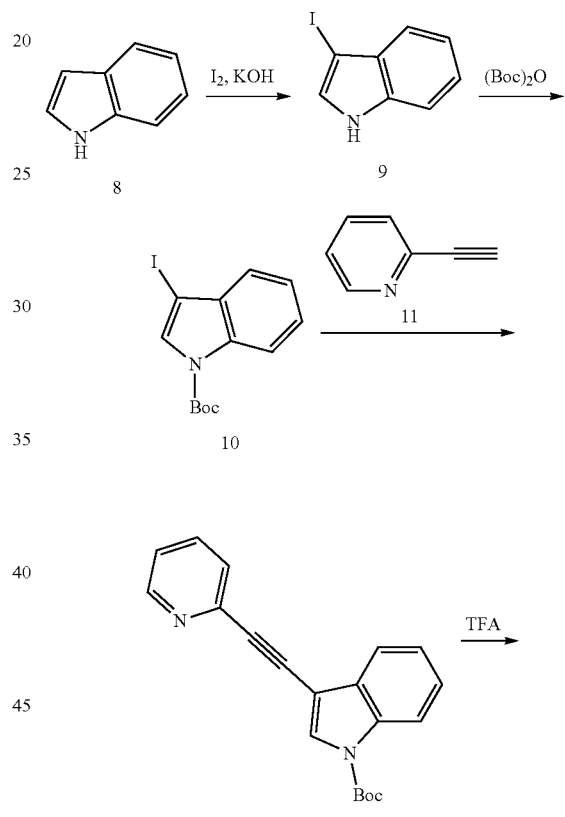

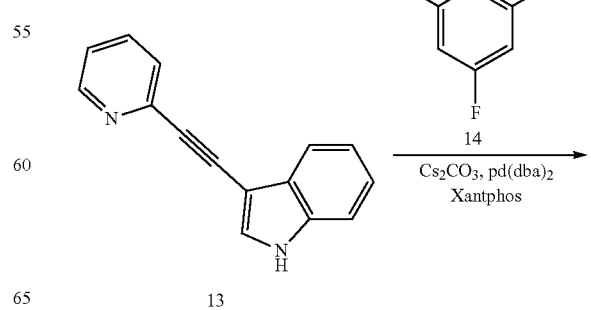

-continued

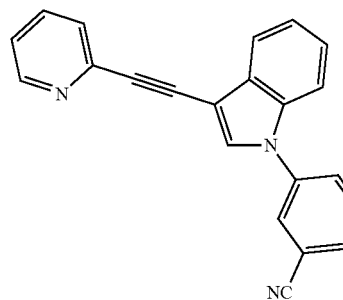

Compound 1

Experimental Section:
Procedure for Preparation of 9:

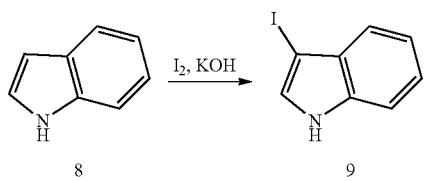

To a solution of 8 (1.0 g, 8.5 mmol) in 10 mL of dry DMF was added KOH (1.4 g, 25.1 mmol) and I$_2$ (2.6 g, 10.2 mmol). The mixture was stirred at room temperature for 1 h. TLC showed the consumption of 8. To the mixture was added aqueous Na$_2$S$_2$O$_4$ (20 mL). After stirring for 10 min, the solution was extracted with EtOAc (2×30 mL). The organic layer was washed with brine (50 mL), dried over anhydrous Na$_2$SO$_4$, filtered and concentrated to give the crude product 9 which was used for the next step directly (2.0 g, yield: 90%).

Procedure for Preparation of 10:

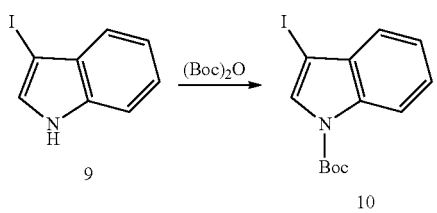 [SMILES: "(Boc)2O" ; Ic1c[nH]c2ccccc12 ; CC(C)(C)OC(=O)n1cc(I)c2ccccc21]

To a solution of 9 (2.0 g, 8.2 mmol) in 20 mL of dry DCM was added Boc$_2$O (2.7 mg, 12.0 mmol) and DMAP (20 mg, 0.12 mmol). The mixture was stirred at room temperature for 1 h. Then the mixture was diluted with water (20 mL) and extracted with DCM (100 mL). The organic layer was washed with brine (50 mL), dried over anhydrous Na$_2$SO$_4$, filtered and concentrated to dryness. The residue was purified by chromatograph column on silica gel to give product 10 (2.3 g, yield: 82%).

$^1$HNMR (400 MHz, CDCl$_3$): 67 1.66 (s, 9 H), 7.29-7.40 (m, 3 H), 7.72 (s, 1 H), 8.12 (d, J=7.6 Hz, 1 H).

Procedure for Preparation of 12:

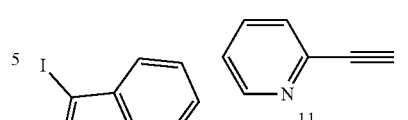

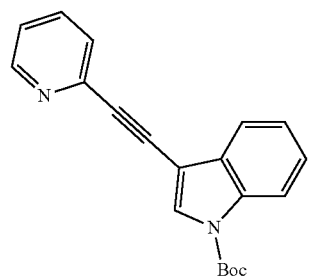

To a solution of 10 (500 mg, 1.5 mmol) in 5 mL of dry dioxane was added 11 (300 mg, 2.9 mmol), CuI (30 mg, 0.15 mmol), Pd(PPh$_3$)$_2$Cl$_2$ (70 mg, 0.15 mmol) and TEA (400 mg, 3.9 mmol). The mixture was degassed under vacuo and purged with N$_2$ for several times. Then the mixture was stirred at 100° C. for 4 h. TLC showed the obtaining of the product. The mixture was concentrated. The crude was washed with water (20 mL) and extracted with EtOAc (80 mL). The organic layer was washed with water and brine, dried over anhydrous Na$_2$SO$_4$ and concentrated. The residue was purified by prep-TLC to give product 12 (450 mg, yield: 94.3%).

LCMS: m/z, 319.1 (M+H)$^+$.

Procedure for Preparation of 13:

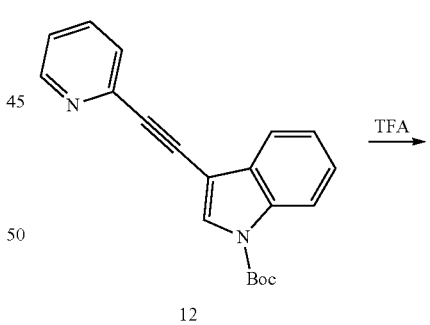

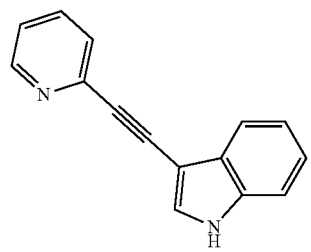

To a solution of 12 (400 mg, 1.25 mmol) in 4 mL of dry DCM was added TFA (1 mL). Then the mixture was stirred at room temperature for 2 h. LCMS showed the obtaining of the product. The mixture was basified by Na$_2$CO$_3$ (20 mL) and extracted with DCM (50 mL). The organic layer was washed with water and brine, dried over anhydrous Na$_2$SO$_4$ and concentrated. The crude product was purified by column chromatograph on silica gel to give product 13 (100 mg, yield: 36.7%).

LCMS: m/z, 219.1 (M+H)$^+$.

Procedure for Preparation of Compound 1:

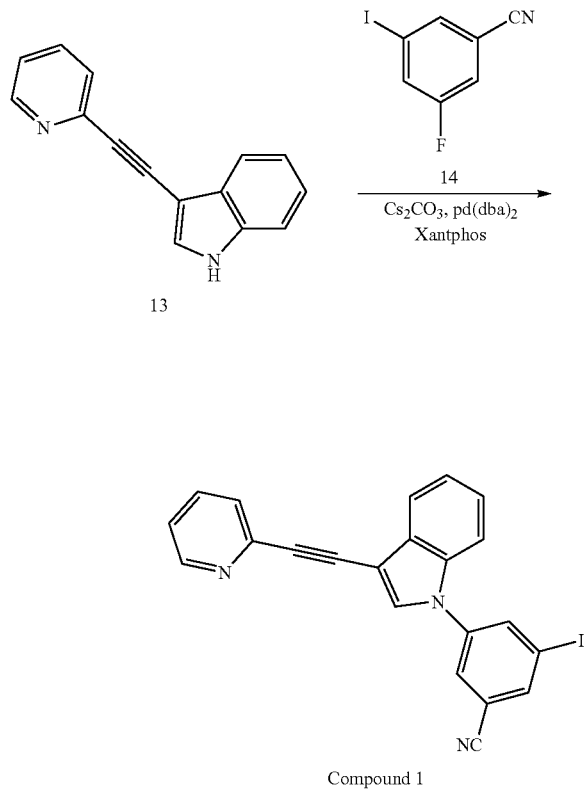

Compound 1

To a solution of 13 (50 mg, 0.2 mmol) in 1 mL of dry DMF was added 14 (53 mg, 0.2 mmol), Cs$_2$CO$_3$ (200 mg, 0.2 mmol), Pd(dba)$_2$ (20 mg) and Xantphos (10 mg). The mixture was degassed under vacuo and purged with N$_2$ for several times. Then the mixture was stirred at 110° C. for 2 h. The mixture was diluted with water (20 mL) and extracted with EtOAc (50 mL). The organic layer was washed with brine (20 mL), dried over anhydrous Na$_2$SO$_4$ and concentrated. The crude product was purified by prep-TLC to give the target product Compound 1 (2.8 mg, yield: 4%).

LCMS: m/z, 445.9 (M+H)$^+$;

$^1$HNMR (400 MHz, CDCl$_3$): δ8.57 (s, 1 H), 8.03 (s, 1H), 7.87 (s, 1H), 7.82-7.83 (m, 1H), 7.71 (m, 1H), 7.58-7.61 (m, 1H), 7.54 (s, 1H), 7.50-7.53 (m, 1H), 7.47-7.50 (m, 1 H), 7.30-7.42 (m, 2H), 7.29-7.28 (m, 1H).

Example Compound 2

Preparation of 3-fluoro-5-(3-(pyridin-2-ylethynyl)-1H-indol-1-yl)benzonitrile

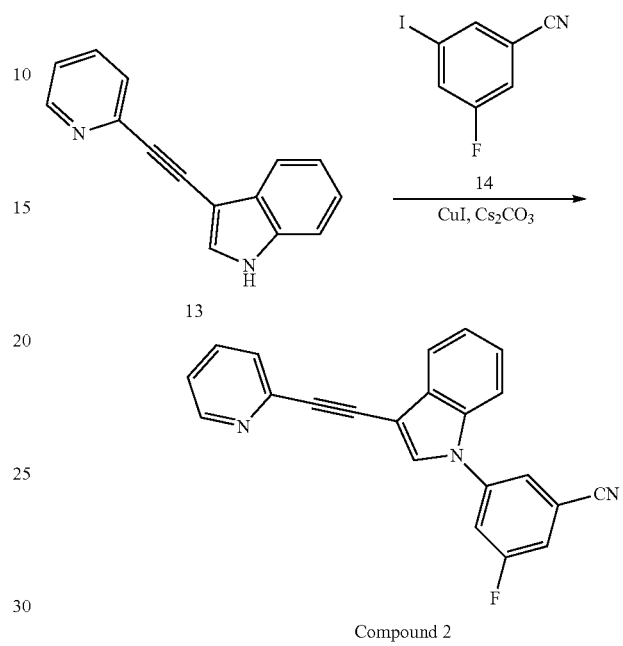

Compound 2

Experimental Section:

Procedure for Preparation of Compound 2:

To a solution of 13 (100.0 mg, 0.46 mmol) and 14 (135.8 mg, 0.55 mmol) in DMSO (2.0 mL) was added CuI (9.5 mg, 0.05 mmol) and Cs$_2$CO$_3$ (399.7 mg, 0.92 mmol) at rt, the mixture was stirred at 100° C. for 10 h under N$_2$ atmosphere. The solution was diluted with EtOAc (10 mL), washed with water, brine (10 mL), dried over anhydrous Na$_2$SO$_4$, filtered and concentrated to dryness. The residue was purified by prep-TLC to afford the target product Compound 2 (5.0 mg, yield: 3.2%).

LCMS: m/z, 338.0 (M+H)$^+$;

$^1$HNMR (400 MHz, CDCl$_3$): δ8.59 (d, J=4.4 Hz, 1H), 7.88 (d, J=6.8 Hz, 1H), 7.59-7.52 (m, 3H), 7.50-7.45 (m, 3H), 7.32-7.28 (m, 3H), 7.19-7.17 (m, 1H).

Example Compound 3

Preparation of 1-(4-fluorophenyl)-3-(pyridin-2-yl-ethynyl)-1H-indole

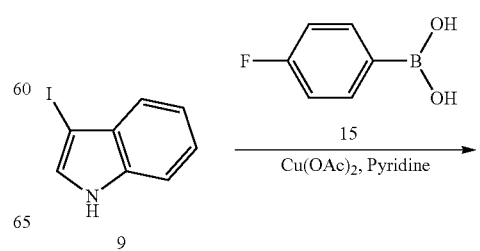

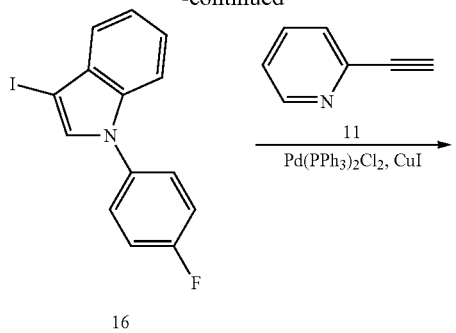

16

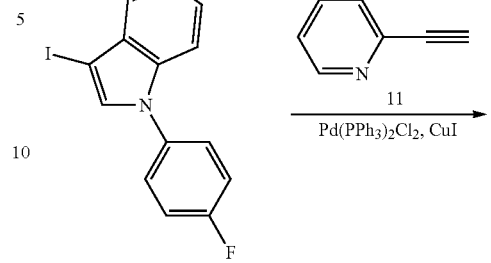

Compound 3

Experimental Section:

Procedure for Preparation of 16:

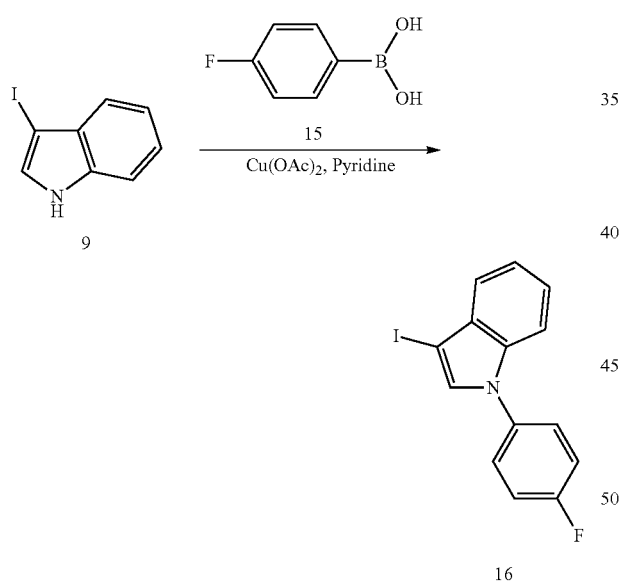

Cu(OAc)$_2$ (362.0 mg, 2.0 mmol) was added to a solution of 15 (243.0 mg, 1.0 mmol), 16 (278.0 mg, 2.0 mmol) and Pyridine (247.0 mg, 3.0 mmol) in DCM (10.0 mL). The reaction mixture was stirred at rt. under O$_2$ balloon overnight. The reaction mixture was filtered and filtration pie was washed with DCM. Combined organic phase was washed with water, dried over anhydrous Na$_2$SO$_4$ and concentrated to dryness. The residue was further purified by column chromatography on silica gel to afford product 17 (200 mg, yield: 62.7%).

$^1$HNMR (400 MHz, CDCl$_3$): δ7.39-7.57 (m, 4 H), 7.23-7.29 (m, 5 H).

Procedure for Preparation of Compound 3:

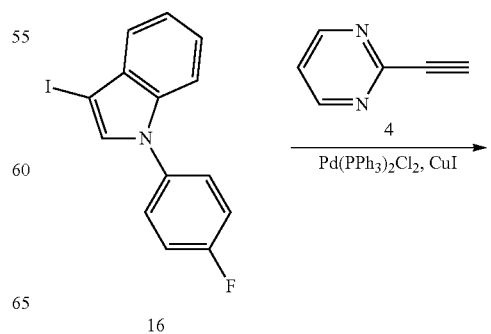

Compound 3

To a solution of 17 (150.0 mg, 0.45 mmol) in 5 mL of dry dioxane was added 11 (91.8 mg, 0.9 mmol), CuI (9.0 mg, 0.03 mmol), Pd(PPh$_3$)$_2$Cl$_2$ (21.0 mg, 0.03 mmol) and TEA (120.0 mg, 1.2 mmol). The mixture was degassed under vacuo and purged with N$_2$ for several times and then stirred at 100° C. for 4 h. The mixture was concentrated to dryness, the crude was dissolved with 10 mL of EA and washed with water. The organic layer was separated, washed with brine, dried over anhydrous Na$_2$SO$_4$ and concentrated. The crude product was purified by prep-TLC to give the desired product Compound 3 (25.0 mg, yield: 20.8%).

LCMS: m/z, 313.1 (M+H)$^+$;

$^1$HNMR (400 MHz, CDCl$_3$): δ8.64 (d, J=4.8 Hz, 1 H), 7.93 (d, J=6.0 Hz, 1 H), 7.53-7.68 (m, 3 H), 7.45-7.48 (m, 3 H), 7.22-7.31 (m, 5 H).

Example Compound 4

Preparation of 1-(4-fluorophenyl)-3-(pyrimidin-2-ylethynyl)-1H-indole

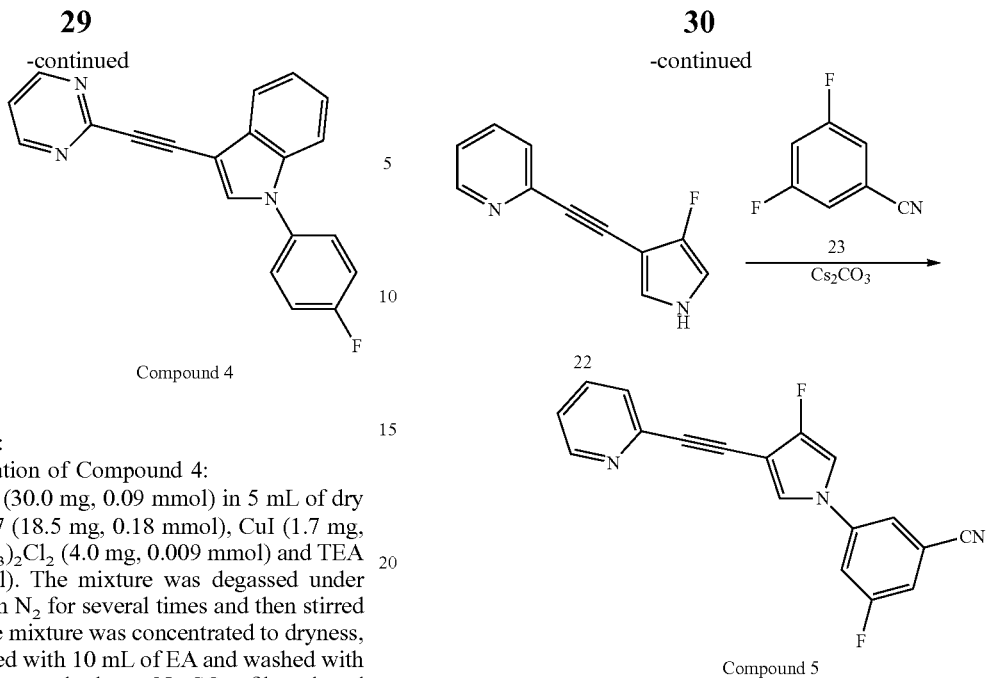

Compound 4

Experimental Section:
Procedure for Preparation of Compound 4:

To a solution of 16 (30.0 mg, 0.09 mmol) in 5 mL of dry dioxane was added 17 (18.5 mg, 0.18 mmol), CuI (1.7 mg, 0.009 mmol), Pd(PPh$_3$)$_2$Cl$_2$ (4.0 mg, 0.009 mmol) and TEA (27.0 mg, 0.27 mmol). The mixture was degassed under vacuo and purged with N$_2$ for several times and then stirred at 100° C. for 4 h. The mixture was concentrated to dryness, the crude was dissolved with 10 mL of EA and washed with water, brine, dried over anhydrous Na$_2$SO$_4$, filtered and concentrated to dryness. The crude product was purified by prep-TLC to give the target product Compound 4 (1.6 mg, yield: 5.7%).

LCMS: m/z, 314.1 (M+H)$^+$;
$^1$HNMR (400 MHz, CDCl$_3$): δ8.69-8.70 (d, J=4.2 Hz, 2 H), 7.91 (d, J=6.0 Hz, 1 H), 7.64 (s, 1 H), 7.33-7.42 (m, 3 H), 7.14-7.24 (m, 5 H).

Example Compound 5

Preparation of 3-fluoro-5-(3-fluoro-4-(pyridin-2-ylethynyl)-1H-pyrrol-1-yl)benzonitrile

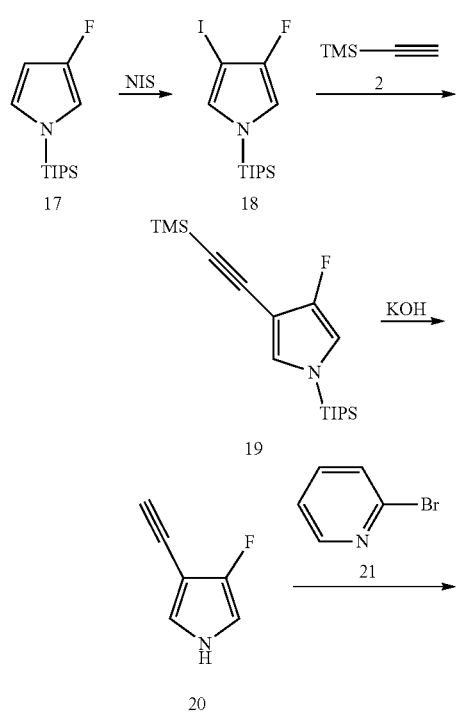

Compound 5

Experimental Section:
Procedure for Preparation of 18:

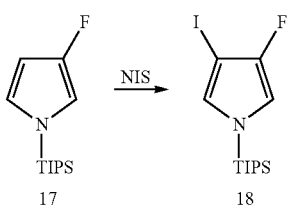

To a solution of 17 (890 mg, 3.69 mmol) in acetone (50 mL) was added NIS (912 mg, 4.06 mmol) at −78° C. Then the reaction mixture was stirred at that temperature for 2 h. LCMS showed that the reaction was completed. The reaction mixture was concentrated and purified by prep-TLC to give the desired product 18 (340 mg, yield: 25%).

LCMS: m/z 368 (M+H)$^+$.
Procedure for Preparation of 19:

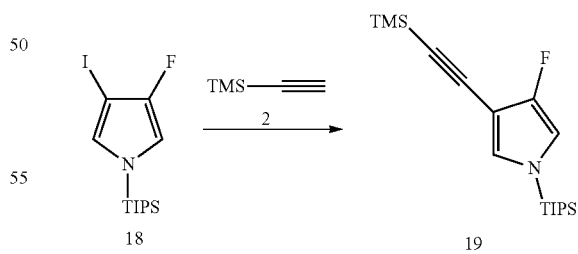

To a solution of 18 (340 mg, 0.93 mmol) in 15 mL of degassed CH$_3$CN was added successively CuI (18 mg, 0.093 mmol), 2 (182 mg, 1.85 mmol), Pd(PPh$_3$)$_2$Cl$_2$ (65 mg, 0.093 mmol) and Et$_3$N (281 mg, 2.78 mmol). The mixture was stirred at 70° C. for 18 h. LCMS showed that the reaction was completed. The reaction mixture was filtered and the filtrate was concentrated and purified by prep-TLC to give the product 19 (220 mg, yield: 70%).

LCMS: m/z 338 (M+H)+.

Procedure for Preparation of 20:

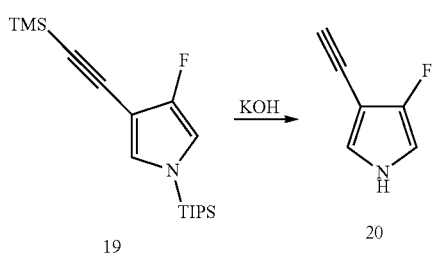

To a solution of 19 (260 mg, 0.77 mmol) in MeOH (10 mL) was added KOH (86 mg, 1.54 mmol). Then the reaction mixture was stirred at rt for 1 h. TLC showed that the reaction was completed. The reaction mixture was quenched with water, extracted with DCM (3×20 mL). The combined organic layer was dried over anhydrous $Na_2SO_4$, concentrated to give product 20 (60 mg, yield: 71%).

Procedure for Preparation of 22:

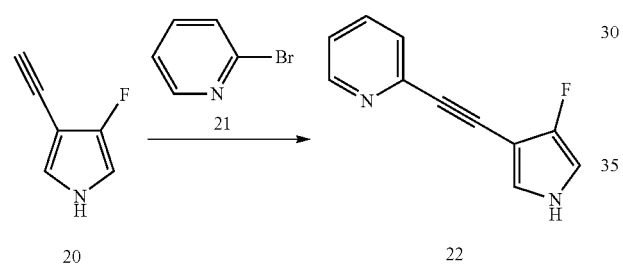

To a solution of compound 20 (60 mg, 0.55 mmol) in 10 mL of degassed $CH_3CN$ was added successively CuI (10 mg, 0.055 mmol), 21 (174 mg, 1.10 mmol), and $Pd(PPh_3)_2Cl_2$ (39 mg, 0.055 mmol) and $Et_3N$ (167 mg, 1.65 mmol). The mixture was stirred at 80° C. for 18 h. LCMS showed that the reaction was completed. The reaction mixture was filtered and the filtrate was concentrated and purified by prep-TLC to give the product 22 (80 mg, yield: 78%).

LCMS: m/z 187 (M+H)+.

Procedure for Preparation of Compound 5:

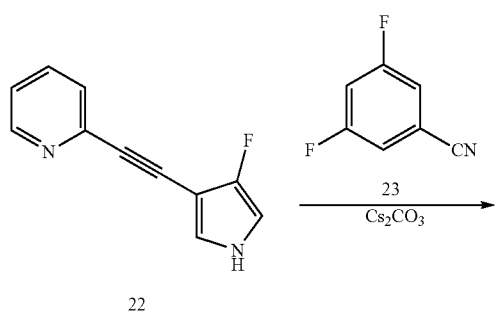

-continued

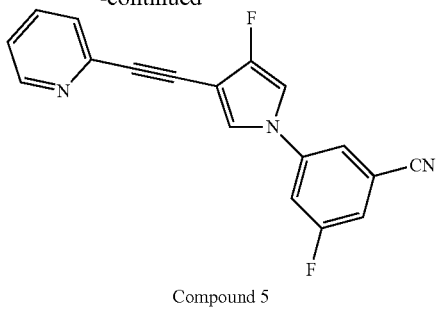

Compound 5

To a solution of 22 (50 mg, 0.27 mmol) in 5 mL of degassed DMF was added successively compound 23 (56 mg, 0.40 mmol) and $Cs_2CO_3$ (175 mg, 0.54 mmol). The mixture was heated at 120° C. and stirred for 2 h. LCMS showed that the reaction was completed. The reaction mixture was filtered and the filtrate was concentrated to give the product Compound 5, which was purified by prep-HPLC (8 mg, yield: 10%).

LCMS: nm/z 306 (M+H)+.

$^1$H NMR (400 MHz, $CDCl_3$): δ 8.62 (d, J=4.0 Hz, 1H), 7.68-7.66 (m, 1H), 7.52-7.50 (m, 1H), 7.42 (s, 1H), 7.30-7.28 (m, 2H), 7.26-7.25 (m, 1H), 7.16-7.15 (m, 1H), 6.86-6.85 (m, 1H).

Example Compound 6

Preparation of 3-fluoro-5-(3-(pyridin-2-ylethynyl)-1H-pyrrol-1-yl)benzonitrile

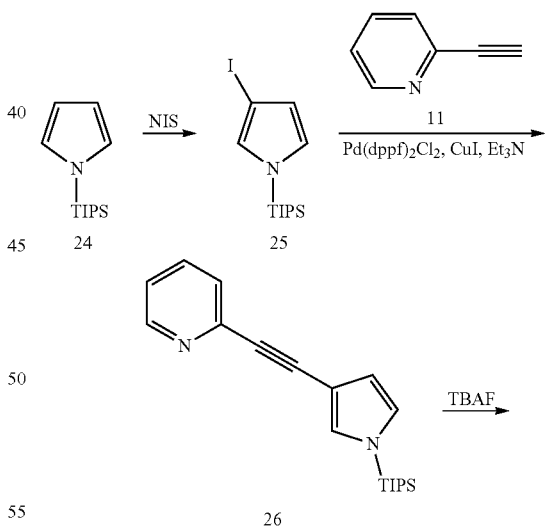

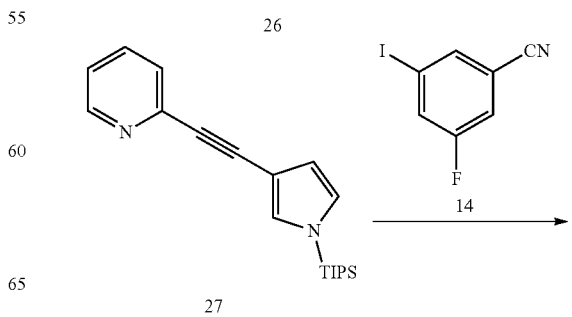

-continued

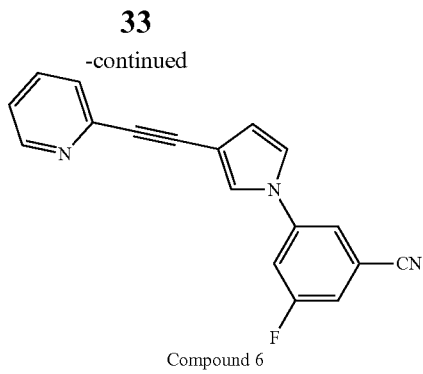

Compound 6

Experimental Section:

Procedure for Preparation of 24:

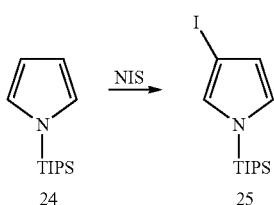

A solution of compound 24 (22 g, 0.10 mol) in 600 mL acetone was cooled to −70° C., NIS (27 g, 0.12 mol) was added, the reaction was stirred 6 h at the same temperature, then warmed to rt and stirred 3 h. After the reaction was completed, concentrated in vacuo to give crude product 25 (10 g, yield: 51.4%), which was used for the next step without purification.

Procedure for Preparation of 25:

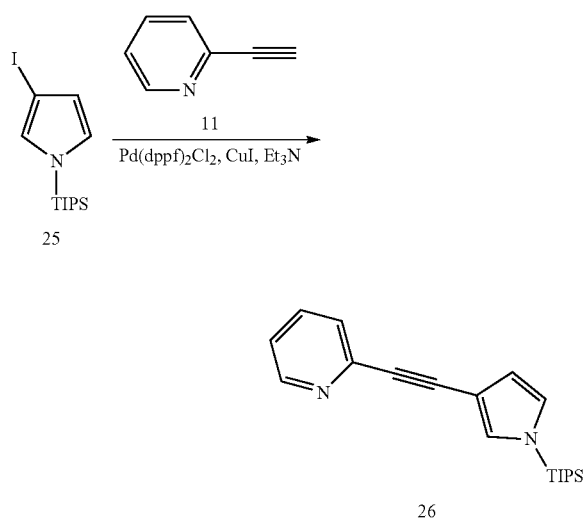

To a solution of 25 (20.4 g, 58.3 mmol) and 11 (4 g, 38.8 mmol) in 200 mL TEA, was added Pd(dppf)$_2$Cl$_2$ (1.3 g, 1.94 mmol) and CuI (740 mg, 3.88 mmol). The mixture was heated to reflux and stirred 4 h, TLC showed the reaction was completed. After cooled to rt. the reaction mixture was concentrated in vacuo, and purified by silica gel column chromatography to give product 26 (4 g, yield: 31.8%).

Procedure for Preparation of 26:

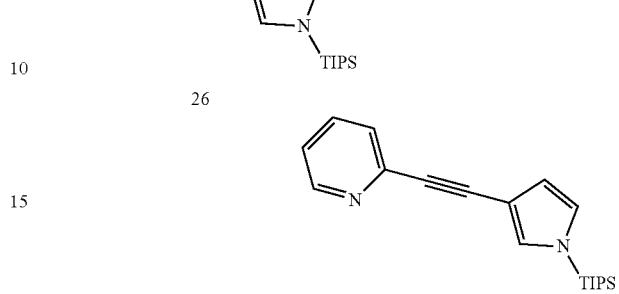

To a solution of 26 (4 g, 12.3 mmol) in 300 mL THF, TBAF (1M in THF) (18.5 mL, 18.5 mmol) was added. The reaction mixture was stirred at rt. for 1 h. Then the mixture was extracted with EA. The combined organic layer was concentrated in vacuo and purified by silica gel column chromatography to give product 27 (1.5 g, yield: 40%).

Procedure for Preparation of Compound 6:

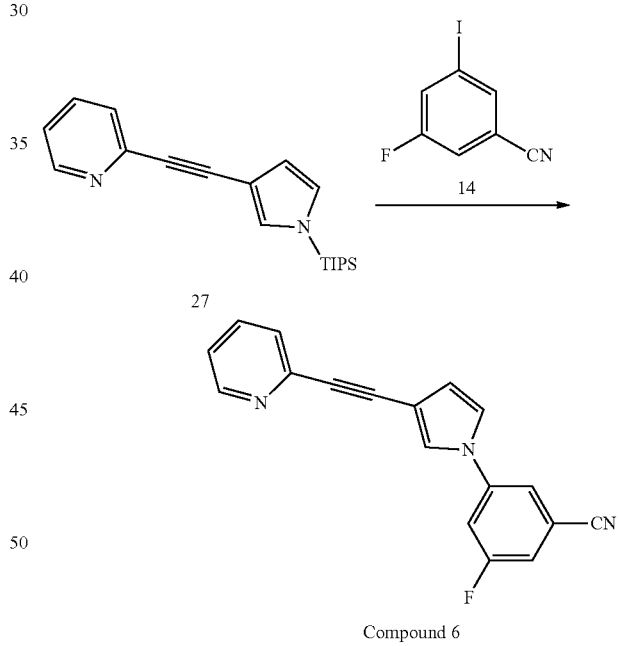

To a solution of 27 in DMSO (40 mL), K$_2$CO$_3$ (1 g, 7.29 mmol), CuI (50 mg, 0.24 mmol), L-proline (50 mg, 0.49 mmol) and 14 (0.9 g, 3.64 mmol) were added successively. The reaction mixture was purged with N$_2$ several times, and heated at 80° C. 6 h under N$_2$ atmosphere. TLC showed the reaction was completed, water (300 mL) was added to the reaction mixture, extracted with EA, and the organic layer was washed with saturated brine, dried over anhydrous Na$_2$SO$_4$, concentrated and purified by silica gel column chromatography to give the target product Compound 6 (140 mg, yield: 20%).

LCMS: m/z 288.4 (M+H)$^+$;

¹H NMR (400M Hz, DMSO-d6): δ8.57 (d, 2H), 8.06 (m, 2H), 8.57 (d, 2H), 7.76-7.82 (m, 2H), 7.68 (t, 1H), 7.54 (d, 1H), 7.35-7.38 (br, 1H), δ 6.59 (s, 1H).

Example Compound 7

Preparation of 1-(4-fluorophenyl)-3-(phenylethynyl)-1H-pyrrole

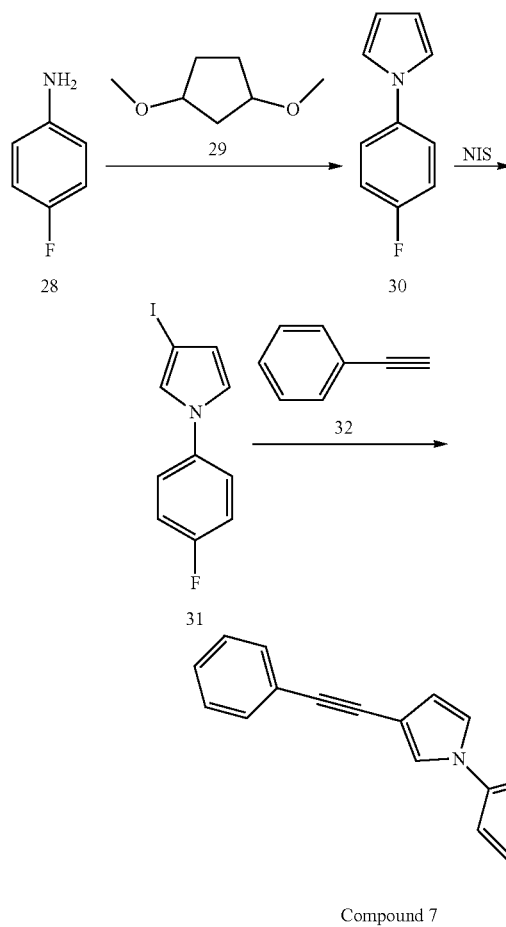

Experimental Section:
Procedure for Preparation of 29:

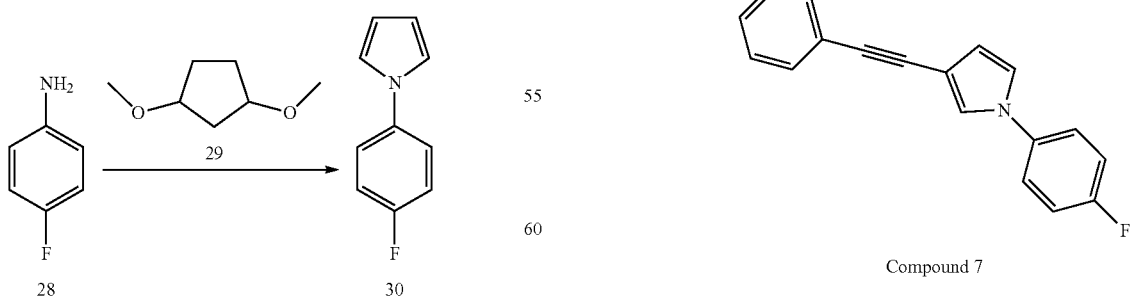

28 (7.14 g, 54.0 mmol) was added to 27 (5 g, 45.0 mmol), then the mixture was stirred at 110-120° C. TLC indicated the reaction was completed. The reaction mixture was extracted with EA. The organic layer was washed with water and brine solution and dried over anhydrous Na₂SO₄. The combined organic layer was evaporated under reduced pressure, and the resulting product was further purified by column chromatography to give target product 30 (1.1 g, yield: 15.17%).

¹H NMR (400 MHz, CDCl₃): δ 7.40-7.32 (m, 2H), 7.17-7.09 (m, 2H), 7.03 (t, J=2.2 Hz, 2H), 6.36 (t, J=2.2 Hz, 2H).

Procedure for Preparation of 31:

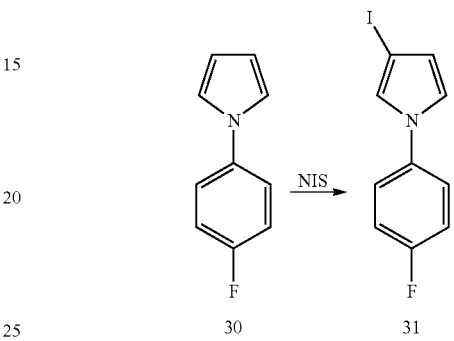

To a solution of 30 (800 mg, 4.96 mmol) in acetone (30 mL) at −78° C., NIS was added (1117 mg, 4.96 mmol) in one portion. The reaction mixture was stirred at −78° C. for 6 h, then warmed to rt over 3 h. EA (30 mL) was added. Washed with water and brine, dried over anhydrous Na₂SO₄. After evaporation of the solvent, the residue was purified by column chromatography to yield the product 31 (355 mg, 24.91%).

Procedure for Preparation of Compound 7:

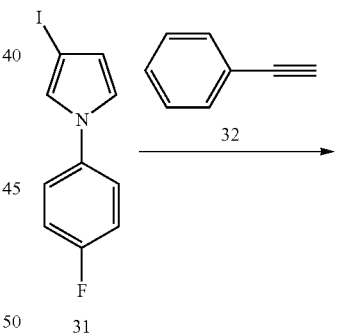

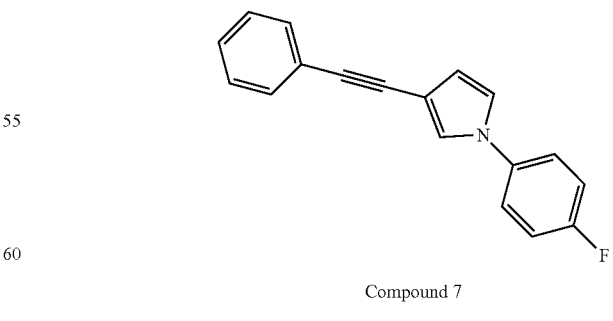

A mixture solution of 31 (100 mg, 0.348 mmol) and 32 (39.1 mg, 0.383 mmol) in 10 mL of TEA in the presence of Pd(PPh₃)₂Cl₂ (12.23 mg, 0.017 mmol) and CuI (6.63 mg, 0.035 mmol) was heated at 65° C. for 5 h under the protection of Ar. The reaction mixture was cooled, concentrated under reduced pressure. The residue was purified by column chromatography to give the target product Compound 7 (10 mg, yield: 10.99%).

LCMS: m/z 262 [M+H]$^+$;

$^1$H NMR (500 MHz, DMSO-d$_6$): δ 7.77 (s, 1H), 7.71-7.63 (m, 2H), 7.49-7.42 (m, 2H), 7.43-7.31 (m, 6H), 6.47 (s, 1H).

Example Compound 8

Preparation of 2-((2,5-dimethyl-1-(4-(trifluoromethoxy)phenyl)-1H-pyrrol-3-yl)ethynyl)pyridine

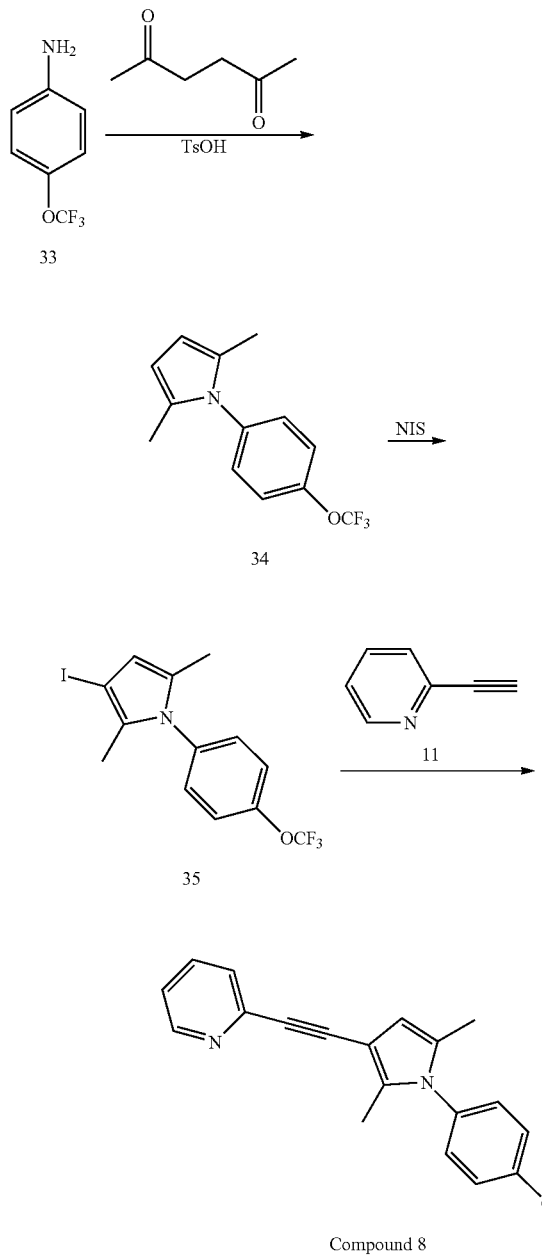

Experimental Section:
Procedure for Preparation of 34:

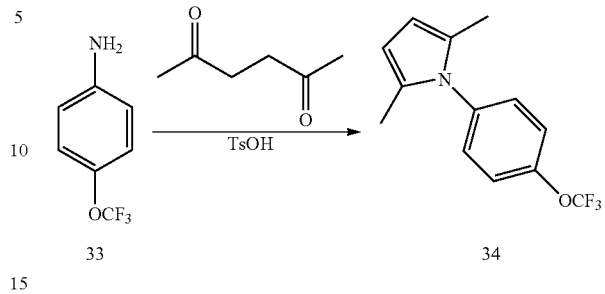

A mixture of hexane-2,5-dione (3.22 g, 28.2 mmol) and 33 (5.0 g, 28.2 mmol) in the presence of TsOH (0.389 g, 2.258 mmol) was heated at 100° C. for 5 h. The reaction mixture was cooled, filtered, and concentrated. The crude material was purified by chromatography to give the target product 34 (5.39 g, yield: 75.0%).

Procedure for Preparation of 35:

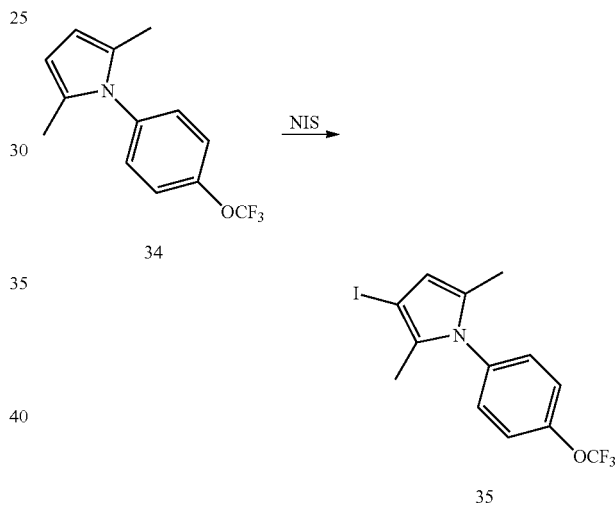

To a solution of 34 (160 mg, 0.627 mmol) in acetone (8 mL) at −78° C. was added NIS (141 mg, 0.627 mmol) in one portion. The reaction mixture was stirred at −78° C. for 6 h, then warmed to rt over 3 h, EA (30 mL) was added, washed with water and brine, dried over anhydrous Na$_2$SO$_4$. After evaporation of the solvent, the residue was purified by column chromatography to give the product 35 (220 mg, yield: 92.1%0).

LCMS: m/z 382 [M+H]$^+$.

Procedure for Preparation of Compound 8:

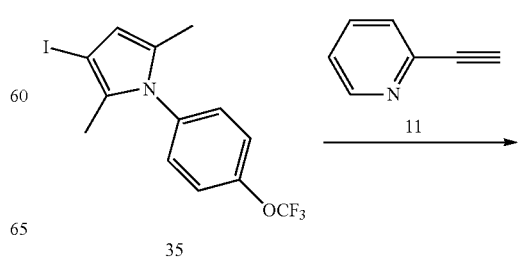

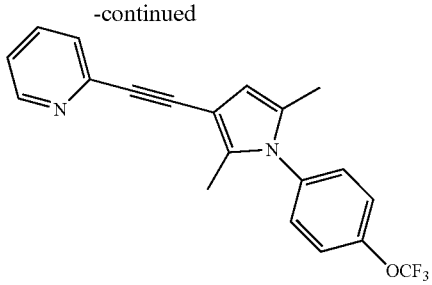

Compound 8

To a solution of 35 (200 mg, 0.525 mmol) and 11 (108 mg, 1.050 mmol) in 6 mL of Et$_3$N and 14 mL DMF, Pd(PPh$_3$)$_2$Cl$_2$ (18.42 mg, 0.026 mmol) and CuI (9.99 mg, 0.052 mmol) were added. The mixture was protected with Ar atmosphere, then was heated to 100° C. for 24 h. TLC analysis showed some starting material was left and a major product was formed. The reaction mixture was then washed with water and concentrated in vacuo. The crude product was purified by silica gel column chromatography to give the target product Compound 8 (25 mg, yield: 13.37%).

LCMS: 357 [M+H]$^+$;

$^1$H NMR (400 MHz, CDCl$_3$): δ 8.58-8.56 (m, 1H), 7.63-7.60 (m, 1H), 7.46-7.44 (m, 1H), 7.34 (d, J=8.4, 2H), 7.25-7.23 (m, 2H), 7.17-7.15 (m, 1H), 6.15 (d, J=1.2 Hz, 1H), 2.19 (s, 3H), 2.00 (s, 3H).

Example Compound 9

Preparation of 2-((2,5-dimethyl-1-(4-(trifluoromethoxy)phenyl)-1H-pyrrol-3-yl)ethynyl)pyrimidine

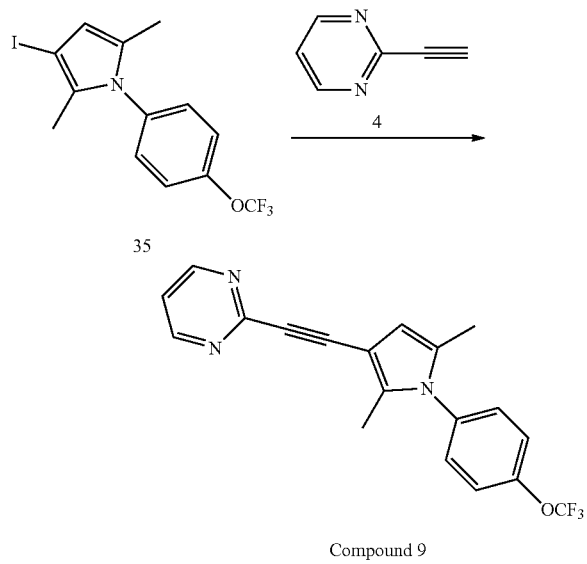

Compound 9

Experimental Section:
Procedure for Preparation of Compound 9:

To a solution of 35 (200 mg, 0.525 mmol) and 4 (109 mg, 1.050 mmol) in 6 mL of Et$_3$N and 14 mL DMF, Pd(PPh$_3$)$_2$Cl$_2$ (18.42 mg, 0.026 mmol) and CuI (9.99 mg, 0.052 mmol) were added. The mixture was protected with Ar atmosphere, then was heated to 100° C. for 24 h. TLC analysis showed some starting material was left and a major product was formed. The reaction mixture was then washed with water and concentrated in vacuo. The crude product was purified by silica gel column chromatography to give the target product Compound 9 (25 mg, yield: 13.33%).

LCMS: m/z 358 (M+H)$^+$;

$^1$H NMR (400 MHz, CDCl$_3$): δ 8.70 (d, J=5.2 Hz, 2H), 7.34 (d, J=8.4 Hz, 2H), 7.27-7.24 (m, 2H), 7.15-7.12 (t, J=4.8 Hz, 1H), 6.20 (d, J=0.8 Hz, 1H), 2.22 (s, 3H), 2.00 (s, 3H).

Example Compound 10

Preparation of 4-((2, 5-dimethyl-1-(4-(trifluoromethoxy)phenyl)-1H-pyrrol-3-yl)ethynyl)pyridine

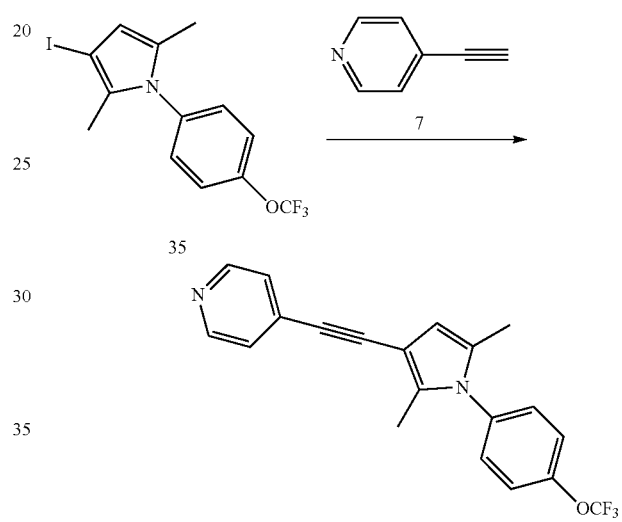

Compound 10

Experimental Section:
Procedure for Preparation of Compound 10:

To a solution of 35 (100 mg, 0.262 mmol) and 7 (54.1 mg, 0.525 mmol) in 6 mL of Et$_3$N and 14 mL DMF, Pd(PPh$_3$)$_2$Cl$_2$ (9.21 mg, 0.013 mmol) and CuI (5.0 mg, 0.026 mmol) were added. The mixture was protected with Ar atmosphere, then was heated to 100° C. for 24 h. TLC analysis showed some starting material was left and a major product was formed. The reaction mixture was then washed with water and concentrated in vacuo. The crude product was purified by silica gel column chromatography to give the target product Compound 10 (25 mg, yield: 26.7%).

LCMS: m/z 357 (M+H)$^+$;

$^1$HNMR (400 MHz, CDCl$_3$): δ 8.54 (br, 2H), 7.34 (t, J=8.2 Hz, 4H), 7.24 (d, J=2.4 Hz, 2H), 6.12 (d, J=0.8 Hz, 1H), 2.16 (s, 3H), 2.01 (s, 3H).

Functional Calcium Flux Assay Methodology

For functional assays, HEK293 cells stably expressing recombinant rat mGluR5 were seeded in 384-well plates and dye loaded using Fluo-8. Cells were then washed to remove the un-incorporated dye. Antagonist evaluation was performed following a 15 min incubation of the test compound followed by the addition of submaximal concentration of glutamate. Intracellular calcium ([Ca$^{2+}$]$_i$) measurements were performed using a fluorometric imaging plate reader (FLIPR, Molecular Devices). The glutamate-evoked increase in $[Ca^{2+}]_i$ in the presence of the test compounds was compared to the response to glutamate alone (the positive control). Antagonist inhibition curves were fitted with a 4-parameter logistic equation giving $IC_{50}$ values, and Hill coefficients using an iterative nonlinear curve fitting algorithm.

The tables below provide IC50 data in this assay. In the activity column, $A=IC_{50} >1,000$ and $\leq 5,000$ nM; $B=IC_{50}>500$ and $\leq 1,000$ nM and $C=IC_{50}\leq 500$ nM.

TABLE 1

| # | Example Compound | Structure | IC50 value (FLIPR assay) |
|---|---|---|---|
| 1 | 1 | 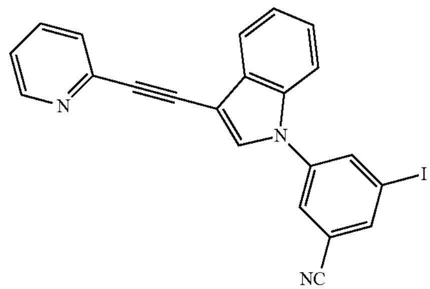 [SMILES: N#Cc1cc(I)cc(-n2cc(C#Cc3ccccn3)c3ccccc32)c1] | C |
| 2 | 2 | 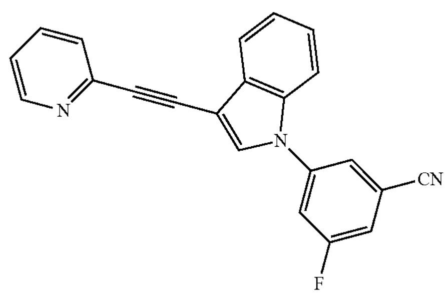 [SMILES: N#Cc1cc(F)cc(-n2cc(C#Cc3ccccn3)c3ccccc32)c1] | C |
| 3 | 3 | 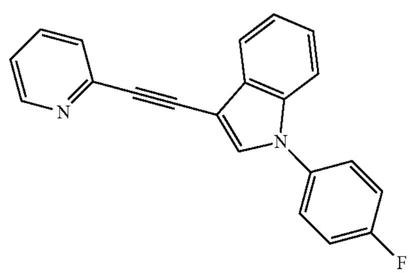 | C |
| 4 | 4 | 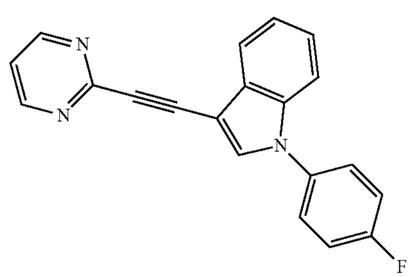 [SMILES: Fc1ccc(-n2cc(C#Cc3ncccn3)c3ccccc32)cc1] | C |

TABLE 1-continued
| # | Example Compound | Structure | IC50 value (FLIPR assay) |
|---|---|---|---|
| 5 | 5 | 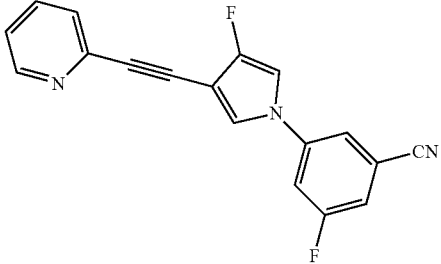 [SMILES: N#Cc1cc(F)cc(-n2cc(F)c(C#Cc3ccccn3)c2)c1] | C |
| 6 | 6 | 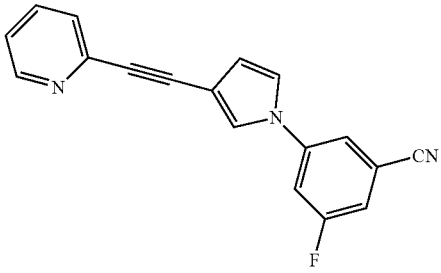 [SMILES: N#Cc1cc(F)cc(-n2ccc(C#Cc3ccccn3)c2)c1] | C |
| 7 | 7 | 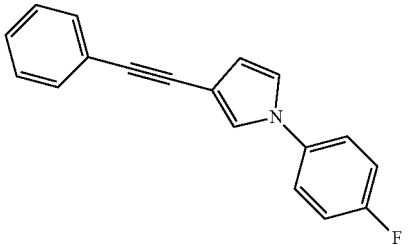 [SMILES: Fc1ccc(-n2ccc(C#Cc3ccccc3)c2)cc1] | C |
| 8 | 8 | 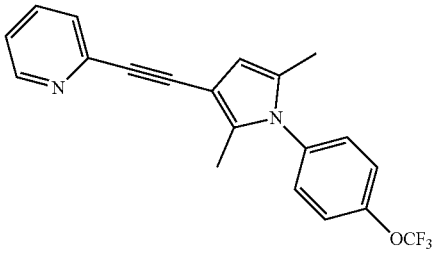 [SMILES: Cc1cc(C#Cc2ccccn2)c(C)n1-c1ccc(OC(F)(F)F)cc1] | C |
| 9 | 9 | 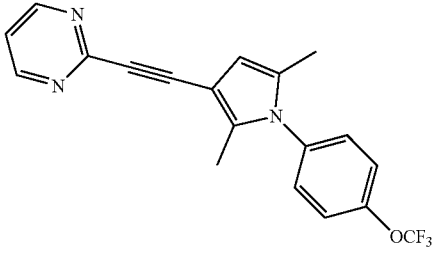 [SMILES: Cc1cc(C#Cc2ncccn2)c(C)n1-c1ccc(OC(F)(F)F)cc1] | C |

TABLE 1-continued

| Example # | Compound | Structure | IC50 value (FLIPR assay) |
|---|---|---|---|
| 10 | 10 | 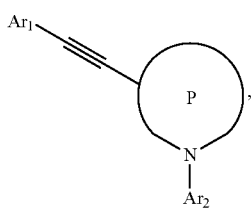 | A |

Example 3

Radioligand Binding Assay Using Membrane Preparations Expressing Rat mGluR5

The radiolabeled allosteric antagonist [$^3$H]-2-Methyl-6-(phenylethynyl)pyridine (MPEP, American Radiolabeled Chemical) was used to evaluate the ability of test compounds to interact with the MPEP site on mGluR5 as described in Rodriguez et al. [Mol Pharmacol 78:1105-1123, 2010]. Membranes were prepared from HEK293 cells expressing rat mGluR5. Radioligand binding assays were performed in 96-well plates (Corning) containing binding buffer (15 mM Tris pH 7.4, 120 mM NaCl, 100 mM KCl, 25 mM MgCl$_2$, 25 mM CaCl$_2$)) with a final assay volume of 250 µL and 40 µg membranes/well.

Saturation isotherms were determined by incubation in presence of 12 increasing concentrations of [$^3$H]-MPEP (0.1-100 nM), while competition experiments were performed with a fixed concentration (4 nM) of [$^3$H]-MPEP in presence of 12 increasing concentrations of test compound (1-30,000 nM). Incubations were performed at 4° C. for 1 h. Nonspecific binding was estimated using 100 µM MTEP. At the end of incubation, membranes were filtered over GF/C filter plates (Perkin Elmer) presoaked in 0.1% BSA for 2 h at room temperature. Filter plates were then washed 5 times with ice cold buffer (15 mM Tris, pH 7.4 plus 0.1% BSA) using the Packard Filtermate Harvester and dried overnight in a 37° C. oven. Fifty µL microscint 20 (PerkinElmer) were added to each well and the plates were incubated on an orbital shaker for 15 min before counting on a Microbeta Trilux for 2 min/well.

It is to be understood that the invention is not limited to the particular embodiments of the invention described above, as variations of the particular embodiments may be made and still fall within the scope of the appended claims.

What is claimed is:
1. A compound of formula I:

(I)

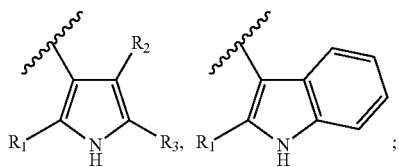

or a pharmaceutically acceptable salt thereof, wherein:
Ar$_1$ is a 5- to 10-membered mono- or bicyclic heteroaryl ring that contains 1-3 heteroatoms selected from the group consisting of N, O and S, wherein the 5- to 10-membered ring system is optionally substituted with 1-3 substituents independently selected from alkyl, halogen, —OH, —CN, nitro, alkoxy, —CF$_3$, —O—CF$_3$, —S(CH$_3$), —O-alkyl, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)heterocycloalkyl, wherein the substituents optionally combine to form an optionally substituted 5-7 membered fused carbacyclic or heterocyclic ring;
Ar$_2$ is a 5- to 10-membered mono- or bicyclic heteroaryl ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)-cycloalkyl, —C(O)-heterocycloalkyl, or substituted lower alkyl wherein the substituents optionally combine to form an optionally substituted 5-7 membered fused carbacyclic or heterocyclic ring, or a 5- to 10-membered mono- or bicyclic aryl ring, wherein the 5- to 10-membered ring system is optionally substituted with 1-3 substituents independently selected from alkyl, —F, —Cl, —Br, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl wherein the substituents optionally combine to form an optionally substituted 5-7 membered fused carbacyclic or heterocyclic ring;
P is a heteroaryl ring selected from and R$_1$, R$_2$ and R$_3$ are independently selected from —H, halogen, —OH, —CN, nitro, alkyl, alkoxy, —CF$_3$, —OCF$_3$, —CH$_2$-aryl, phenyl, heteroaryl, alkanoyl, —O-aryl, —O—CH$_2$-aryl, —N(CH$_3$)$_2$, —C(O)-cycloalkyl, —C(O)-heterocycloalkyl, —C(O)O-alkyl, —C(O)O-aryl, wherein the substituents optionally combine to form an optionally substituted 5-7 membered fused carbacyclic or heterocyclic ring.

2. The compound according to claim 1, of structure Ia, wherein:

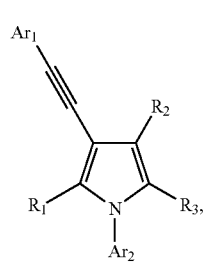

(Ia)

or a pharmaceutically acceptable salt thereof,
wherein:

Ar$_1$ is a 5- to 10-membered mono- or bicyclic heteroaryl ring that contains 1-3 heteroatoms selected from the group consisting of N, O and S, wherein the 5- to 10-membered ring system is optionally substituted with 1-3 substituents independently selected from alkyl, -halogen, —OH, —CN, nitro, alkoxy, —CF$_3$, —O—CF$_3$, —S(CH$_3$), —O-alkyl, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)heterocycloalkyl, wherein the substituents optionally combine to form an optionally substituted 5-7 membered fused carbacyclic or heterocyclic ring;

Ar$_2$ is a 5- to 10-membered mono- or bicyclic heteroaryl ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, 13 O—CH$_2$-aryl, —N(CH$_3$)$_2$, cycloalkyl, heterocycloalkyl, —C(O)cycloalkyl, —C(O)-heterocycloalkyl, or substituted lower alkyl wherein the substituents optionally combine to form an optionally substituted 5-7 membered fused carbacyclic or heterocyclic ring, or a 5- to 10-membered mono- or bicyclic aryl ring, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl wherein the substituents optionally combine to form an optionally substituted 5-7 membered fused carbacyclic or heterocyclic ring; and R$_1$, R$_2$ and R$_3$ are independently selected from —H, halogen, —OH, —CN, nitro, alkyl, alkoxy, —CF$_3$, —OCF$_3$, —CH$_2$-aryl, phenyl, heteroaryl, alkanoyl, —O-aryl, —O—CH$_2$-aryl, —N(CH$_3$)$_2$, —C(O)-cycloalkyl, —C(O)-heterocycloalkyl, —C(O)O-alkyl, —C(O)O-aryl, wherein the substituents optionally combine to form an optionally substituted 5-7 membered fused carbacyclic or heterocyclic ring.

3. The compound according to claim 2 or a pharmaceutically acceptable salt thereof, wherein:

Ar$_1$ is a substituted or unsubstituted ring selected from the following list:

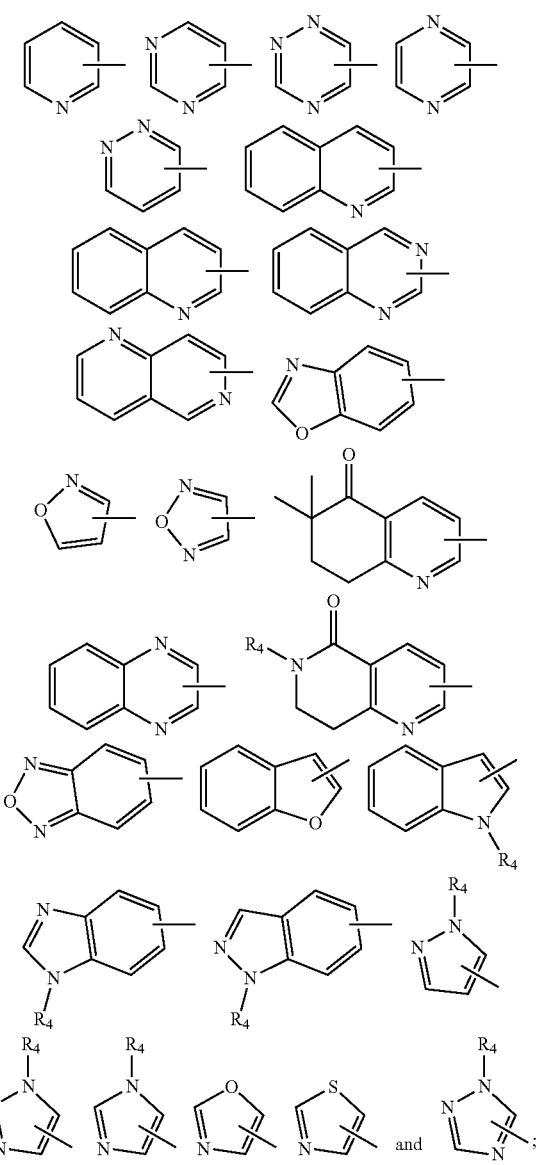

R$_4$ is —H or lower alkyl;

Ar$_2$ is a 5- to 10-membered mono- or bicyclic heteroaryl ring that contains 1-3 heteroatoms independently selected from the group consisting of N, O and S, wherein the 5-to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S- alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl wherein the substituents optionally combine to form an optionally substituted 5-7 membered fused carbacyclic or heterocyclic ring, or a 5- to 10-membered mono- or bicyclic aryl ring, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl wherein the substituents optionally combine to form an optionally substituted 5-7 membered fused carbacyclic or heterocyclic ring; and R$_1$, R$_2$ and R$_3$ are independently selected from —H, halogen, —OH, —CN, nitro, alkyl, alkoxy, —CF$_3$, —OCF$_3$, —CH$_2$-aryl, phenyl, heteroaryl, alkanoyl, —O-aryl, —O—CH$_2$-aryl, —N(CH$_3$)$_2$, —C(O)-cycloalkyl, —C(O)-heterocycloalkyl, —C(O)O-alkyl, —C(O)O-aryl, wherein the substituents optionally combine to form an optionally substituted 5-7 membered fused carbacyclic or heterocyclic ring.

4. The compound according to claim 3 or a pharmaceutically acceptable salt thereof, wherein:

Ar$_i$ is 2-pyridinyl or substituted 2-pyridinyl;

Ar$_2$ is optionally mono- or disubstituted mono- or bicyclic aryl, optionally mono- or disubstituted mono- or bicyclic heteroaryl; and R$_1$, R$_2$ and R$_3$ are independently selected from —H, halogen, —OH, —CN, nitro, alkyl, alkoxy, —CF$_3$, —OCF$_3$, —CH$_2$-aryl, phenyl, heteroaryl, alkanoyl, —O -aryl, —O—CH$_2$-aryl, —N(CH$_3$)$_2$, —C(0)-cycloalkyl, —C(O)-heterocycloalkyl, —C(O)O-alkyl, —C(O)O-aryl, wherein the substituents optionally combine to form an optionally substituted 5-7 membered fused carbacyclic or heterocyclic ring.

5. The compound according to claim 3 or a pharmaceutically acceptable salt thereof, wherein:

Ar$_1$ is 2-pyridinyl, 4-pyridinyl, or pyrimidinyl;

Ar$_2$ is a 5- to 10-membered mono- or bicyclic aryl or heteroaryl ring that contains 1, 2, or 3 heteroatoms independently selected from the group consisting of N, O and S, wherein the 5- to 10-membered ring system is optionally substituted with 1-3 substituents independently selected from —C$_1$-C$_4$-alkyl, —F, —Cl, —Br, —OH, —CN, nitro, —CF$_3$, —OCF$_3$, —O—C$_1$-C$_4$-alkyl, —SCH$_3$, —S(O)—CH$_3$, —S(O$_2$)—CH$_3$, —CO$_2$CH$_3$, —C(O)NH$_2$, —C(O)NH(CH$_3$), —C(O)N(CH$_3$)$_2$, and phenyl; and R$_1$, R$_2$ and R$_3$ are independently selected from —H, halogen and —CH$_3$.

6. The compound according to claim 1, of formula Ib,

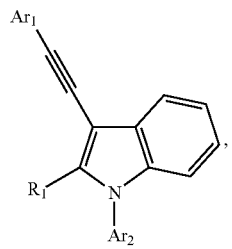

(Ib)

or a pharmaceutically acceptable salt thereof, wherein:

Ar$_1$ is an unsubstituted or substituted ring selected from the following list:

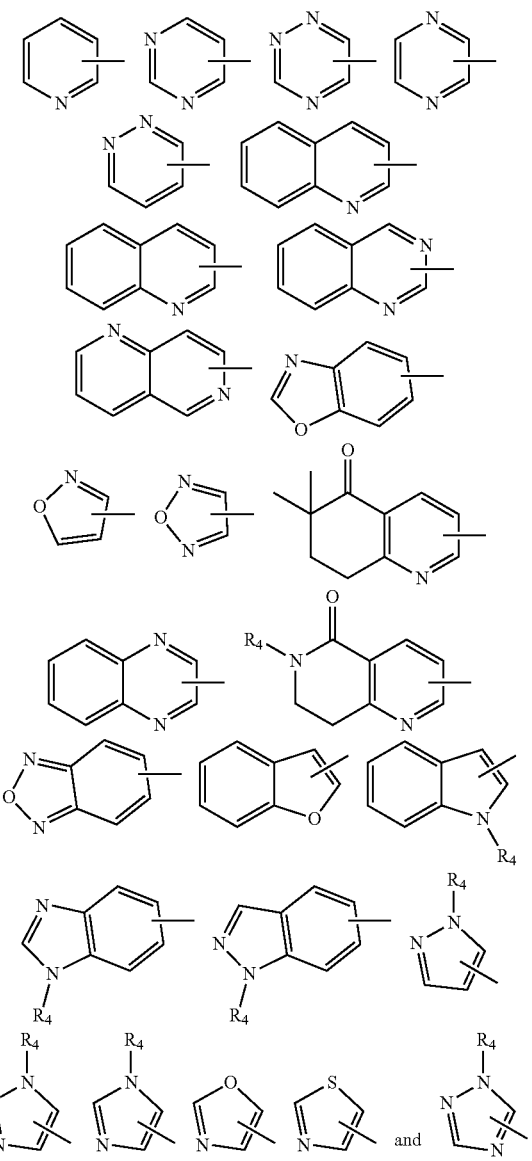

R$_4$ is —H or lower alkyl;

Ar$_2$ is a 5- to 10-membered mono- or bicyclic heteroaryl ring that contains 1-3 heteroatoms independently selected from the group consisting of N, O and S, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl or a 5- to 10-membered mono- or bicyclic aryl ring, wherein the 5- to 10-membered ring system is optionally substituted with 1-3 substituents independently selected from alkyl, halogen, —OH, —CN, nitro, alkoxy, —CF$_3$, —OCF$_3$, —S(CH$_3$), —OCH$_3$, —S-alkyl, —S(O)-alkyl, —S(O$_2$)-alkyl, —S(O$_2$)-aryl, —CH$_2$-aryl, heteroaryl, alkanoyl, —O-aryl, —O—CH$_2$-aryl, —N(CH$_3$)$_2$, cycloalkyl, heterocycloalkyl, —C(O)cycloalkyl, —C(O)-heterocycloalkyl, or substituted lower alkyl; and R$_1$ is independently selected from —H, halogen, —OH, —CN, nitro, alkyl, alkoxy, —CF$_3$, —OCF$_3$, —CH$_2$-aryl, phenyl, heteroaryl, alkanoyl, —O-aryl, —O—CH$_2$-aryl, —N(CH$_3$)$_2$, —C(O)-cycloalkyl, —C(O)-heterocycloalkyl, —C(O)O-alkyl, —C(O)O-aryl.

7. The compound according to claim 5 or a pharmaceutically acceptable salt thereof, wherein:

Ar$_1$ is 2-pyridinyl or substituted 2-pyridinyl;

Ar$_2$ is optionally mono- or disubstituted mono- or bicyclic aryl, optionally mono- or disubstituted mono- or bicyclic heteroaryl; and R$_1$ is H.

8. The compound according to claim 6 or a pharmaceutically acceptable salt thereof, wherein:

Ar$_1$ is 2-pyridinyl optionally substituted with 1 or 2 substituents independently selected from C$_1$-C$_4$-alkyl;

Ar$_2$ is a 5- to 10-membered mono- or bicyclic aryl or heteroaryl ring that contains 1-3 heteroatoms independently selected from the group consisting of N, O and S, wherein the 5- to 10-membered ring system is optionally substituted with 1, 2 or 3 substituents independently selected from —C$_1$-C$_4$-alkyl, halogen, —OH, —CN, nitro, —CF$_3$, —OCF$_3$, —O—C$_1$-C$_4$-alkyl, —SCH$_3$, —S(O)—CH$_3$, —S(O$_2$)—CH$_3$, —CO$_2$CH$_3$, —C(O)NH$_2$, —C(O)NH(CH$_3$), —C(O)N(CH$_3$)$_2$, and phenyl; and R$_1$ is H.

9. The compound according to claim 1 or a pharmaceutically acceptable salt thereof, wherein said compound is:

3-iodo-5-(3-(pyridin-2-ylethynyl)-1H-indo-1-1-yl)benzonitrile, 3-fluoro-5-(3-(pyridin-2-ylethynyl)-1H-indo-1-1-yl)benzonitrile, 1-(4-fluorophenyl)-3-(pyridin-2-ylethynyl)-1H-indole, 1-(4-fluorophenyl)-3-(pyrimidin-2-ylethynyl)-1H-indole, 3-fluoro-5-(3-fluoro-4-(pyridin-2-ylethynyl)-1H-pyrrol-1-yl)benzonitrile, 3-fluoro-5-(3-(pyridin-2-ylethynyl)-1H-pyrrol-1-yl)benzonitrile, 2-((2,5-dimethyl-1-(4-(trifluoromethoxy)phenyl)-1H-pyrrol-3-yl)ethynyl)pyridine, 2-((2,5-dimethyl-1-(4-(trifluoromethoxy)phenyl)-1H-pyrrol-3-yl)ethynyl)pyrimidine, or 4-((2, 5-dimethyl-1-(4-(trifluoromethoxy)phenyl)-1H-pyrrol-3-yl)ethynly)pyridine.

10. A pharmaceutical composition, comprising a compound according to claim 1 in free base or pharmaceutically acceptable salt form, in association with a pharmaceutical carrier or diluent.

11. The compound according to claim 5, wherein the C$_1$-C$_4$-alkyl is selected from the group consisting of methyl, ethyl, n-propyl, iso-propyl, n-butyl, iso-butyl and tent-butyl.

12. The compound according to claim 5, wherein the —O—C$_1$-C$_4$-alkyl is selected from the group consisting of methoxy, ethoxy, n-propoxy, iso-propoxy, n-butoxy, iso-butoxy, and tert-butoxy.

13. The compound according to claim 5, wherein the 5- to 10-membered ring system is phenyl.

14. The compound according to claim 8, wherein the C$_1$-C$_4$-alkyl is selected from the group consisting of methyl, ethyl, n-propyl, iso-propyl, n-butyl, iso-butyl, and tent-butyl.

15. The compound according to claim 8, wherein the —O—C$_1$-C$_4$-alkyl is selected from group consisting of methoxy, ethoxy, propoxy, iso-proxy, n-butoxy, iso-butoxy, and tert-butoxy.

16. The compound according to claim 8, wherein the 5- to 10-membered ring system is phenyl.

* * * * *